US012797224B2

(12) United States Patent
Perez et al.

(10) Patent No.: US 12,797,224 B2
(45) Date of Patent: Nov. 17, 2026

(54) ORTHOPEDIC BRACE HAVING AN ADJUSTABLE SPINAL SUPPORT EXTENSION AND SUPPORT HARNESS

(71) Applicant: Aspen Medical Products, LLC, Irvine, CA (US)

(72) Inventors: Joel Perez, Long Beach, CA (US); Geoffrey Wong, Costa Mesa, CA (US); Duane Romo, Aliso Viejo, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 533 days.

(21) Appl. No.: 17/984,101

(22) Filed: Nov. 9, 2022

(65) Prior Publication Data

US 2023/0149199 A1 May 18, 2023

Related U.S. Application Data

(60) Provisional application No. 63/279,650, filed on Nov. 15, 2021.

(51) Int. Cl.
*A61F 5/02* (2006.01)

(52) U.S. Cl.
CPC .............. *A61F 5/028* (2013.01); *A61F 5/026* (2013.01)

(58) Field of Classification Search
CPC .......... A61F 5/026; A61F 5/028; A61F 5/022; A61F 5/024; A61F 5/01; A61F 5/02–03; A44B 13/00; A44B 13/0029; A44B 13/0058; A44B 13/0076; A45F 3/00; A45F 3/04–10
USPC ........................................................... 602/19
See application file for complete search history.

(56) References Cited

U.S. PATENT DOCUMENTS

| | | | |
|---|---|---|---|
| 3,533,106 | A | 10/1970 | Kremp |
| 4,492,225 | A | 1/1985 | Picolet et al. |
| 6,969,363 | B2 | 11/2005 | Houser |
| 6,971,996 | B2 | 12/2005 | Houser |
| 7,150,721 | B2 | 12/2006 | Houser |

(Continued)

FOREIGN PATENT DOCUMENTS

| | | | | |
|---|---|---|---|---|
| DE | 102017108839 A1 * | 10/2018 | .............. | A61F 5/02 |
| EP | 162763 B1 | 10/1988 | | |

(Continued)

OTHER PUBLICATIONS

Espacenet_EnglishTranslation_DE102017108839A.*

(Continued)

*Primary Examiner* — Rachael E Bredefeld
*Assistant Examiner* — Seth R. Brown
(74) *Attorney, Agent, or Firm* — Rutan & Tucker, LLP

(57) ABSTRACT

An orthopedic brace features a belt brace and an adjustable spinal support extension. The belt brace includes a structural member. The adjustable spinal support extension is configured for insertion into the structural member. The adjustable spinal support extension includes a sleeve, a first strut member, and a second strut member adjustably coupled to the first strut member to alter a length of the spinal support extension. The first strut member and the second strut member are partially enclosed within the sleeve and a fastener of the structural member is attachable to a fastener on the sleeve when the adjustable spinal support extension is placed within the sleeve.

18 Claims, 19 Drawing Sheets

(56) References Cited

U.S. PATENT DOCUMENTS

| | | | |
|---|---|---|---|
| 7,662,121 | B2 | 2/2010 | Zours |
| 8,187,337 | B2 | 5/2012 | Kremser et al. |
| 8,327,669 | B2 | 12/2012 | Weihermueller |
| D678,089 | S | 3/2013 | Doppel et al. |
| 8,409,299 | B2 | 4/2013 | Kurth |
| 8,448,531 | B2 | 5/2013 | Schneider |
| 8,476,172 | B2 | 7/2013 | Christof |
| 8,512,268 | B2 | 8/2013 | Weihermueller |
| 8,540,781 | B2 | 9/2013 | Nissels et al. |
| 8,845,567 | B2 | 9/2014 | Herresthal |
| 8,887,402 | B2 | 11/2014 | Doppel et al. |
| 9,180,026 | B2 | 11/2015 | Shen |
| 9,220,626 | B2 | 12/2015 | Petiot et al. |
| 9,370,440 | B2 | 6/2016 | Ingimundarson et al. |
| 9,393,132 | B2 | 7/2016 | Kranner et al. |
| 9,506,172 | B2 | 11/2016 | Atmanspacher |
| 9,572,705 | B2 | 2/2017 | Ingimundarson et al. |
| 9,642,766 | B2 | 5/2017 | Lipshaw et al. |
| 9,707,132 | B2 | 7/2017 | Richardson et al. |
| 9,750,643 | B2 | 9/2017 | Convert et al. |
| 9,795,171 | B2 | 10/2017 | Lipshaw et al. |
| 10,117,618 | B2 | 11/2018 | Richardson et al. |
| 10,117,784 | B2 | 11/2018 | Lipshaw et al. |
| 10,159,589 | B2 | 12/2018 | Bauer |
| 10,238,572 | B2 | 3/2019 | Chardon-Bras et al. |
| 10,285,897 | B2 | 5/2019 | Chardon-Bras et al. |
| 10,307,281 | B2 | 6/2019 | Sorg et al. |
| D854,173 | S | 7/2019 | Violeau et al. |
| 10,344,408 | B2 | 7/2019 | Herold-Herrmann et al. |
| 10,494,747 | B2 | 12/2019 | Atmanspacher |
| 10,501,874 | B2 | 12/2019 | Kostian |
| 10,709,631 | B2 | 7/2020 | Larmer et al. |
| 10,898,365 | B2 | 1/2021 | Ingimundarson et al. |
| 10,918,557 | B2 | 2/2021 | Richardson et al. |
| 10,966,855 | B2 | 4/2021 | Cooney |
| 10,973,698 | B2 | 4/2021 | Lipshaw et al. |
| 10,980,675 | B2 | 4/2021 | Lipshaw et al. |
| 11,098,421 | B2 | 8/2021 | Atmanspacher |
| 11,131,044 | B2 | 9/2021 | Convert et al. |
| 11,149,380 | B2 | 10/2021 | Schott |
| 11,160,678 | B2 | 11/2021 | Waldsich |
| 11,253,384 | B2 * | 2/2022 | Petursson ............. A61F 5/0123 |
| 2005/0192522 | A1 | 9/2005 | Houser |
| 2010/0061796 | A1 | 3/2010 | Kurth |
| 2010/0100197 | A1 | 4/2010 | Kremser et al. |
| 2011/0040222 | A1 | 2/2011 | Weihermueller |
| 2011/0083475 | A1 | 4/2011 | Weihermueller |
| 2011/0112656 | A1 | 5/2011 | Kurth |
| 2011/0144768 | A1 | 6/2011 | Kremser et al. |
| 2011/0152737 | A1 | 6/2011 | Burke et al. |
| 2011/0160631 | A1 | 6/2011 | Herresthal |
| 2011/0229113 | A1 | 9/2011 | Kurth et al. |
| 2012/0035519 | A1 | 2/2012 | Thelemann |
| 2012/0046760 | A1 | 2/2012 | Nissels et al. |
| 2012/0304476 | A1 | 12/2012 | Doppel et al. |
| 2013/0079892 | A1 | 3/2013 | Imhof |
| 2013/0261767 | A1 | 10/2013 | Kranner et al. |
| 2013/0264157 | A1 | 10/2013 | Shen |
| 2013/0268091 | A1 | 10/2013 | Shen |
| 2013/0305788 | A1 | 11/2013 | Atmanspacher |
| 2013/0317404 | A1 | 11/2013 | Bauer et al. |
| 2014/0057234 | A1 | 2/2014 | Nink-Grebe |
| 2014/0128993 | A1 | 5/2014 | Shen |
| 2014/0316312 | A1 | 10/2014 | Atmanspacher |
| 2015/0335457 | A1 | 11/2015 | Bauer |
| 2016/0000595 | A1 | 1/2016 | Sorg et al. |
| 2016/0143750 | A1 | 5/2016 | Kranner et al. |
| 2016/0166410 | A1 | 6/2016 | Dressler et al. |
| 2017/0073860 | A1 | 3/2017 | Rockstroh et al. |
| 2017/0073861 | A1 | 3/2017 | Herold-Herrmann et al. |
| 2017/0119585 | A1 | 5/2017 | Gallien et al. |
| 2017/0156911 | A1 * | 6/2017 | Ingimundarson ....... A61F 5/026 |
| 2017/0172835 | A1 | 6/2017 | Richardson et al. |
| 2017/0247822 | A1 | 8/2017 | Atmanspacher |
| 2017/0273851 | A1 | 9/2017 | Larmer et al. |
| 2017/0335495 | A1 | 11/2017 | Kostian |
| 2017/0354544 | A1 | 12/2017 | Lipshaw et al. |
| 2018/0163328 | A1 | 6/2018 | Hoffeins et al. |
| 2018/0266023 | A1 | 9/2018 | Atmanspacher |
| 2019/0015261 | A1 | 1/2019 | Lipshaw et al. |
| 2019/0021895 | A1 | 1/2019 | Breuil et al. |
| 2019/0029866 | A1 * | 1/2019 | Stier ........................ A61F 5/026 |
| 2019/0046115 | A1 | 2/2019 | Richardson et al. |
| 2019/0125017 | A1 | 5/2019 | Waldsich |
| 2019/0231605 | A1 | 8/2019 | Lipshaw et al. |
| 2019/0298583 | A1 | 10/2019 | Hoffeins |
| 2019/0330795 | A1 | 10/2019 | Schott |
| 2020/0085604 | A1 | 3/2020 | Schöbel et al. |
| 2020/0115830 | A1 | 4/2020 | Atmanspacher |
| 2020/0179150 | A1 | 6/2020 | Lipshaw et al. |
| 2020/0240053 | A1 | 7/2020 | Schmidt et al. |
| 2020/0249657 | A1 | 8/2020 | Schaumber |
| 2020/0268543 | A1 | 8/2020 | Santaniello et al. |
| 2020/0270388 | A1 | 8/2020 | Huger et al. |
| 2020/0347530 | A1 | 11/2020 | Tannebaum |
| 2021/0038437 | A1 | 2/2021 | Lipshaw et al. |
| 2021/0059849 | A1 * | 3/2021 | Yip ......................... A61F 5/026 |
| 2021/0121311 | A1 | 4/2021 | Bauer |
| 2021/0121595 | A1 | 4/2021 | Bauer |
| 2021/0161745 | A1 | 6/2021 | Richardson et al. |
| 2021/0205146 | A1 | 7/2021 | Lipshaw et al. |
| 2021/0267810 | A1 | 9/2021 | Scelles et al. |
| 2021/0274874 | A1 | 9/2021 | Atmanspacher et al. |
| 2021/0275394 | A1 | 9/2021 | Lipshaw et al. |
| 2021/0282955 | A1 | 9/2021 | Cooney |
| 2021/0298401 | A1 | 9/2021 | Thelemann |
| 2021/0338485 | A1 | 11/2021 | Lipshaw |
| 2021/0395931 | A1 | 12/2021 | Convert et al. |

FOREIGN PATENT DOCUMENTS

| | | | |
|---|---|---|---|
| EP | 475811 | A1 | 3/1992 |
| EP | 562967 | B1 | 6/1997 |
| EP | 591024 | B1 | 7/1998 |
| EP | 1266947 | B1 | 8/2004 |
| EP | 1661515 | A2 | 5/2006 |
| EP | 1750625 | A1 | 2/2007 |
| EP | 1050287 | B1 | 7/2007 |
| EP | 917864 | B1 | 8/2007 |
| EP | 2075361 | A1 | 7/2009 |
| EP | 1086669 | B1 | 12/2010 |
| EP | 2314260 | A1 | 4/2011 |
| EP | 1761218 | B1 | 6/2011 |
| EP | 1791453 | B1 | 10/2011 |
| EP | 2316390 | B1 | 3/2012 |
| EP | 1713352 | B2 | 7/2013 |
| EP | 2366330 | B1 | 11/2014 |
| EP | 2815728 | B1 | 1/2016 |
| EP | 2760411 | B1 | 12/2017 |
| EP | 2977031 | B1 | 1/2018 |
| EP | 3138539 | B1 | 5/2018 |
| EP | 2594233 | B1 | 2/2019 |
| EP | 3090709 | B1 | 5/2019 |
| EP | 3117808 | B1 | 10/2019 |
| EP | 3575463 | A1 | 12/2019 |
| EP | 3620562 | A1 | 3/2020 |
| EP | 3530241 | B1 | 8/2020 |
| EP | 3536285 | B1 | 5/2021 |
| EP | 3831994 | A1 | 6/2021 |
| EP | 3838049 | A1 | 6/2021 |
| EP | 3699342 | B1 | 11/2021 |
| WO | 1998034571 | A1 | 8/1998 |
| WO | 2000047147 | A1 | 8/2000 |
| WO | 2001005339 | A1 | 1/2001 |
| WO | 2005112840 | A3 | 6/2007 |
| WO | 2007077368 | A3 | 9/2007 |
| WO | 2007098898 | A3 | 11/2007 |
| WO | 2008152294 | A1 | 12/2008 |
| WO | 2008142331 | A3 | 1/2009 |
| WO | 2007035960 | A3 | 4/2009 |
| WO | 2009092932 | A1 | 7/2009 |
| WO | 2009135474 | A1 | 11/2009 |
| WO | 2010061095 | A1 | 6/2010 |
| WO | 2010072957 | A1 | 7/2010 |

(56) References Cited

FOREIGN PATENT DOCUMENTS

| | | | |
|---|---|---|---|
| WO | 2011086315 | A1 | 7/2011 |
| WO | 2012136845 | A1 | 10/2012 |
| WO | 2013004633 | A1 | 1/2013 |
| WO | 2013144490 | A1 | 10/2013 |
| WO | 2013189831 | A1 | 12/2013 |
| WO | 2014019883 | A1 | 2/2014 |
| WO | 2014155014 | A1 | 10/2014 |
| WO | 2015132409 | A1 | 9/2015 |
| WO | 2016116230 | A1 | 7/2016 |
| WO | 2017167956 | A1 | 10/2017 |
| WO | 2017168095 | A1 | 10/2017 |
| WO | 2017216624 | A1 | 12/2017 |
| WO | 2020115127 | A1 | 6/2020 |
| WO | 2020126181 | A1 | 6/2020 |
| WO | 2020161064 | A1 | 8/2020 |
| WO | 2020161066 | A1 | 8/2020 |
| WO | 2020185199 | A1 | 9/2020 |
| WO | 2020200576 | A1 | 10/2020 |
| WO | 2020234362 | A1 | 11/2020 |
| WO | 2020245114 | A1 | 12/2020 |
| WO | 2020245212 | A1 | 12/2020 |
| WO | 2020245220 | A1 | 12/2020 |
| WO | 2021004726 | A1 | 1/2021 |
| WO | 2021099251 | A1 | 5/2021 |
| WO | 2021204729 | A1 | 10/2021 |
| WO | 2021228833 | A1 | 11/2021 |

OTHER PUBLICATIONS

PCT/US2022/049814 filed Nov. 15, 2021 International Search Report and Written Opinion dated Mar. 3, 2023.

EP 22893710.8 filed Jun. 17, 2024 Extended European Search Report dated Sep. 18, 2025.

* cited by examiner

ORTHOPEDIC BRACE HAVING AN ADJUSTABLE SPINAL SUPPORT EXTENSION AND SUPPORT HARNESS

CROSS-REFERENCE TO RELATED APPLICATION

This application claims the benefit of priority on U.S. Provisional Patent Application No. 63/279,650 filed Nov. 15, 2021, the entire contents of which are incorporated by reference herein.

FIELD

Embodiments of the disclosure relate to the field of medical devices. More specifically, one embodiment of the disclosure relates to an orthopedic brace and components thereof.

GENERAL BACKGROUND

The following description includes information that may be useful in understanding the present invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. A typical orthosis commonly has at least two portions, a rigid portion supporting a body part, and a flexible portion securing the orthosis to the body. One type of orthopedic brace is referred to as a "thoraco-lumbo-sacral orthosis" or by the acronym "TLSO."

A TLSO is a brace that provides support from a mid-portion to a lower portion of the spine. In particular, a "TLSO" is a brace that limits movement in a wearer's spine from the thoracic area (mid-back area) to the wearer's sacrum (lower-back area). At the same time, the TLSO allows a wearer's neck to move freely. This type of brace is normally used to provide support and stabilization of the spine after a back injury and/or surgery, and in some cases, may be utilized to address spinal pathologies.

As compression fractures become more common, especially as our population ages, the use of TLSOs is becoming more prevalent. One common problem experienced by orthotists in connection with conventional TLSOs is that they can be difficult to adjust for wearers to ensure proper fit, where proper fit of the orthosis normally provides the wearer with improved pain reduction and promotes healing.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

Figure 1:
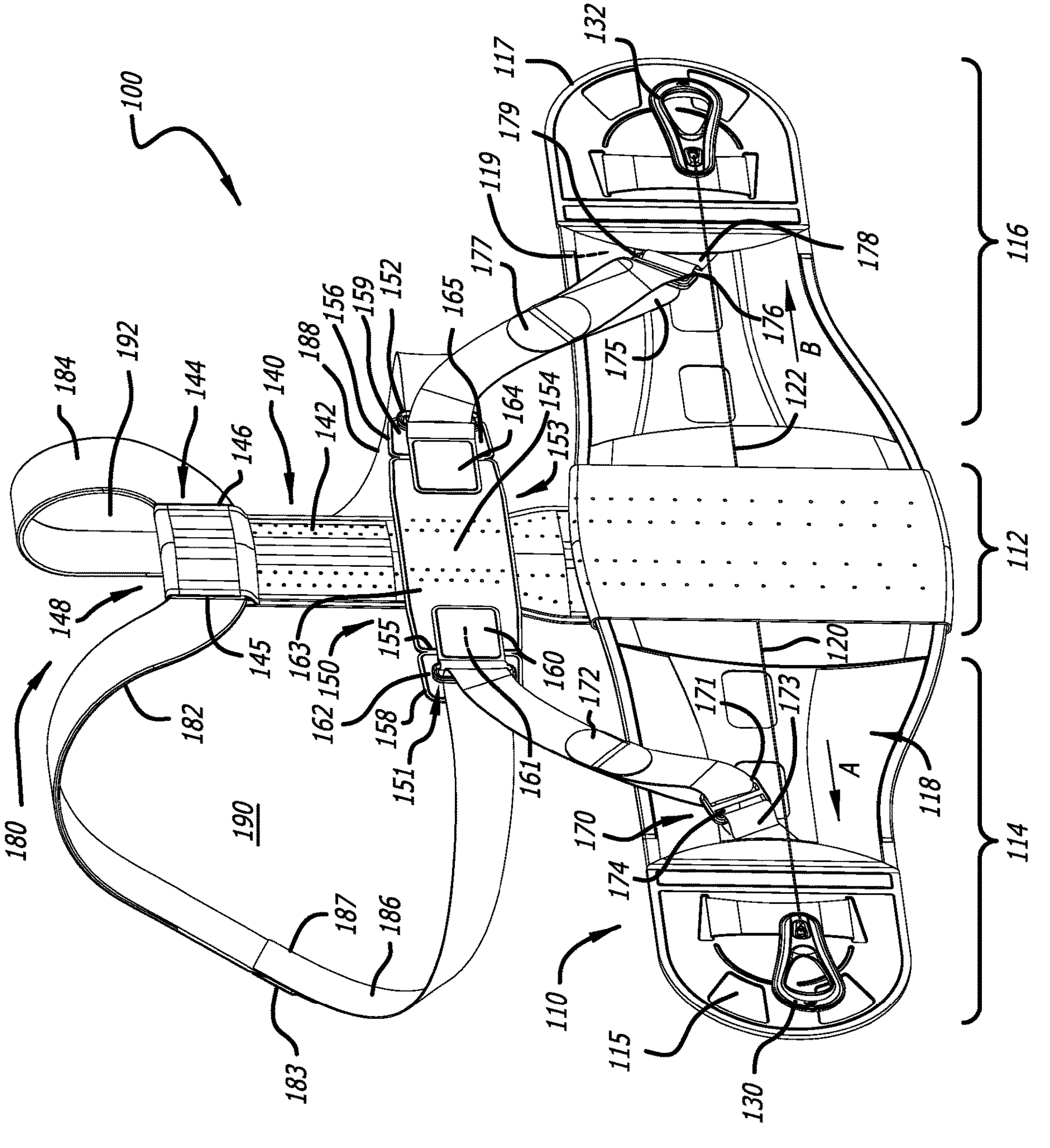
FIG. 1 is an exemplary embodiment of a perspective rear view of an orthopedic brace with an adjustable, spinal support extension and an adjustable support harness.

Embodiments of the present disclosure generally relate to an orthopedic brace having an adjustable spinal support extension and a strap adjustment member, coupled to a posterior surface of the adjustable spinal support extension, for adjusting a support harness for improved comfort when worn. Herein, the orthopedic brace features a belt brace worn around a waist of a wearer, where the belt brace features a structural member located in a lumbar support region of the belt brace to secure a spinal support extension thereto. The spinal support extension, when secured by the structural member, is substantially orthogonal to an orientation of the belt brace. As a result, the orthopedic brace operates as a thoraco-lumbo-sacral orthosis (TLSO) brace with the spinal support extension positioned along a mid-sagittal plane.

More specifically, according to one embodiment of the disclosure, the orthopedic brace features a lumbar sacral orthosis (LSO) type belt brace to be worn around the waist. Oriented to reside within a traverse plane when worn, the belt brace includes a lumbar support disposed between a first lateral support and a second lateral support. The lumbar support is configured to extend across a sagittal plane and be applied to a lower back of the wearer. Each of the first and second lateral supports includes a plurality of fasteners and are configured to wrap around the waist of the wearer and fasten to one another at or near the abdomen. For this embodiment, the fasteners may be arranged as complementary hook and loop fasteners, although other suitable fasteners may be utilized such as snaps, buttons, clasps, or any other fasteners that allow for the belt brace to comfortably fit users of different shapes and sizes.

On an anterior side of the lumbar support of the brace, a structural member is provided to secure the adjustable spinal support extension as described below. According to one embodiment of the disclosure, the structural member includes a partially-enclosed, recessed area sized to receive a first end of the spinal support extension. For instance, the structural member may include, but is not limited or restricted to a pocket formed by soft goods such as one or more layers of textiles, fabrics (inclusive of woven fabrics and/or non-woven fabrics), or other materials capable of being configured as a recessed area to secure and maintain the first end of the spinal support extension. Herein, the pocket may include a fastener at its opening to attach to an anterior surface of a sleeve including an adjustable strut forming the spinal support extension, as described below.

More specifically, the spinal support extension includes an adjustable strut that can be vertically (longitudinally) adjusted to increase or decrease its length based on the height of the wearer. One embodiment of the adjustable strut includes a second strut member configured to be slidably engaged with a first strut member. The second strut member includes a first portion located proximate to a first (upper) end of the adjustable strut and a second (lower) portion located proximate to a second end of the adjustable strut, where the first portion is constructed with a narrower width than the second portion. This narrowing is to allow the spinal support extension to rest comfortably between the shoulder blades of the wearer. Both the first strut member and the second strut member include apertures, which are formulated along their longitudinal center axes and are equivalent in size and shape to align when positioned adjacent to and partially overlapping each other.

After being set to a desired length, the adjustable strut may be partially inserted into the sleeve, namely a soft good having a partially-enclosed retention area. The partially-enclosed retention area includes an enclosed area to which a first end of straps for the harness are attached and an opening to receive and surround a significant portion of the adjustable strut. Depending on the selected length of the adjustable strut, a portion of that adjustable strut may extend from the sleeve prior to placement into (and covering by) the pocket. The sleeve includes a tab located on its anterior surface for insertion through aligned apertures of the first strut member and/or the second strut member (or under a bottom edge of the first strut member) and subsequent attachment to a posterior surface of the sleeve. The portion of the tab and corresponding portion of the posterior surface of the sleeve may include complementary fasteners, such as complementary hook and loop fasteners for example.

The strap adjustment member includes a multi-region panel including a center region disposed between lateral regions that are pivotally coupled to opposite edges of the center region. The pivotal couplings allow for either or both of these lateral regions to be folded toward the center region (or cut and remove) to reduce the sizing of the strap adjustment member to accommodate narrow-bodied wearers. Strap guides may include looped attachment members with a fastener positioned along an anterior surface of the fastener for attachment to a posterior surface of the multi-region panel. Each of the strap guides is adapted with an opening to enable a corresponding strap of the harness to pass through the strap guide so as to form a loop between a top region of the sleeve and the strap guide. Hence, the straps may be used as shoulder straps for the orthopedic brace. The straps continue to be propagated to the belt brace for coupling to a second pair of strap guides attached to the belt brace.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature "loop" type fasteners or other variants to which a "hook" type fastener may be attached. In other situations, the member may be soft goods attached to another structural component of the orthopedic brace such as a textile or fabric sewn to form a partially-enclosed retention area.

The term "partially-enclosed" may be applicable to a structure having a sealed or enclosed perimeter except for at least one opening at selected location along the periphery. As a result, a partially-enclosed retention area is a structure that is configured to encapsulate some of all of a member inserted therein, thereby operating as a pocket, a chamber, a cavity, a hollow area, a lumen, or the like.

The term "attach" and other tenses of the term (attached, attaching, etc.) may be construed as physically connecting a first member to a second member. A "fastener" may be construed as any physical component that is used to attach different members together. An illustrative example of different types of fasteners and fastening techniques may include, but are not limited or restricted to snaps, buttons, clasps, adhesives, sewing, heat sealing (or melting), gluing, knitting, or other physical coupling techniques such as a hook and loop connection.

The terms "rigid" or "rigidity" with respect to a member or portion of a member may be construed as the member being configured to at least partially resist bending or deformation. According to this definition, different lengths of a given structure and composition can be rigid at a shorter length, and flexible at a longer length. As used herein, the term "high rigidity" with respect to a member or portion of a member may be construed as the member will be permanently deformed if bent or twisted by at least 20° end to end.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive. The symbol "/" between two reference numerals references the presence of alternative structures that can be utilized in the same fashion.

As this invention is susceptible to embodiments of many different forms, it is intended that the present disclosure is to be considered as an example of the principles of the invention and not intended to limit the invention to the specific embodiments shown and described.

II. Brace Architecture

Referring device to FIG. 1, an exemplary embodiment of a perspective view of an orthopedic brace 100 with an adjustable spinal support extension 140 and a strap adjustment member 150, which is coupled to a posterior surface 142 of a sleeve portion of the adjustable spinal support extension 140 for adjustment of a support harness 180, is shown. Herein, the orthopedic brace 100 features a belt 110 that is oriented to generally reside within a traverse plane when worn around a waist of a wearer (hereinafter referred to as a "belt brace 110"). The belt brace 110 features a structural member (not shown), which is disposed on a lumbar support 112 of the belt brace 110 and configured to secure the spinal support extension 140. The spinal support extension 140, when secured by the structural member, is oriented to be substantially orthogonal to the traverse plane inclusive of the belt brace 110. As a result, the orthopedic brace 100 may operate as a thoraco-lumbo-sacral orthosis (TLSO) brace with the spinal support extension 140 positioned along a sagittal plane, such as the mid-sagittal plane for this embodiment.

More specifically, the belt brace 110 includes the lumbar support 112 disposed between a first lateral support 114 and a second lateral support 116. The lumbar support 112 is configured to extend across a sagittal plane and be applied to a lower back of the wearer. According to one embodiment of the disclosure, the first lateral support 114 may include one or more fasteners 115 positioned on a posterior side 118 of the belt brace 110 while the second lateral support 116 may include one or more fasteners 117 positioned on an anterior side 119 of the belt brace 110. The first and second lateral supports 114 and 116 are configured to wrap around the waist of the wearer and fasten to one another at or near the abdomen. According to this embodiment, the fastener(s) 115 may be attached to a portion of the second lateral support 116 along the anterior side 119 of the belt brace 110 and the fastener(s) 117 may be attached to a portion of the first lateral support 114 along the posterior side 118 of the belt brace 110.

Alternatively, it is contemplated that both of the fastener(s) 115 and 117 may be positioned on the posterior side 118 of the first lateral support 114 and the second lateral support 116, respectively. For this alternative embodiment, the fastener(s) 115 and 117 may be arranged as complementary fasteners, such as complementary loop and hook fasteners for example, which become attached when the first and second lateral supports 114 and 116 are wrapped around the waist of the wearer.

The belt brace 110 further features a first and second cords 120 and 122 that are threaded through a tightening mechanism (e.g. cord guides, pulleys, etc.) disposed on the lumbar support 112 and/or lateral supports 114/116 of the brace belt 100. Coupled to the tightening mechanism (not shown), the first cord 120 can be pulled in a direction A to tighten the brace belt 110 when worn. Similarly, the second cord 122, coupled to the tightening mechanism (not shown), can be pulled in a direction B to tighten the brace belt 110 when worn. These cords 120 and 122 may be pulled concurrently (i.e., at least partially overlapping in time) to tighten the belt brace 110 by shortening an exposed length of the lumbar support 112. Once a desired level of tightness is achieved, fasteners of the pull tabs 130 and 132 may engage complementary fasteners on the lateral supports 114 and 116. The complementary fasteners may be positioned at selected areas on the posterior side 118 of the belt brace 110.

As shown, the spinal support extension 140 extends longitudinally from the lumbar support 112 of the belt brace 110 along a sagittal plane. The spinal support extension 140 includes a first end 144 and a second end 147 (see FIG. 3B). The first end 144 of the spinal support extension 140 is attached to the support harness 180, namely a first strap member 182 and a second strap member 184. Both the first and second strap members 182 and 184 extend from opposite lateral edges 145 and 146 of the first end 144. Herein, according to one embodiment of the disclosure, the first and second strap members 182 and 184 may be configured as knit tubes composed of a light weight, elastic material. As an illustrative example, the light weight, elastic material may include foam and a light, flexible synthetic or polyolefin resin such as high density polyethylene (HDPE). In particular, for this example, the light weight, elastic material may be comprised of foam and 1/32-inch HDPE. This composition is selected to provide a comfortable, breathable strap that retains a raised shape and contour even when not in use.

The first and second strap members 182 and 184 are attached to a third strap member 186 and a fourth strap member 188, respectively. As one attachment scheme, a first edge 183 of the first strap member 182 may be attached (e.g., sewn) to a first end 187 of the third strap 186. Additionally, a first edge 185 of the second strap member 184 may be attached (e.g., sewn) to a first end 189 of the fourth strap member 188 as shown in detail in FIG. 3B. The third and fourth strap members 186 and 188 may be configured as nylon straps with double-sided loop surfaces, which possesses a different material composition and lesser thickness than the first and second strap members 182 and 184 comprised of foam and HDPE. The third and fourth strap members 186 and 188 are inserted through respective strap guides 151 and 152 (e.g., D-rings, O-rings, etc.) being part of the strap adjustment member 150.

The strap adjustment member 150 includes a multi-region panel 153, which includes a center panel 154 disposed between lateral panels 158 and 159. The lateral panels 158 and 159 are pivotally attached to opposite edges 155 and 156 of the center panel 154. These lateral panels 158 and 159 are trimmable based on these pivotal attachments, which enable either or both of these lateral panels 158 and/or 159 to be folded toward the center panel 154 and attached thereto (or cut and removed). This construction provides an effective and efficient customization scheme for orthotists to reduce the sizing of the strap adjustment member 150 to accommodate more narrowly-bodied wearers.

A first strap guide 151 may be removably attached to the multi-region panel 153 via a secondary strap 160 having at least an anterior side 161 with a "hook" type fastener (not shown) for attachment to a posterior side 162 of the first lateral panel 158 and/or a posterior side 163 of the center panel 154 with a "loop" type fastener. The secondary strap 160 is inserted through the first strap guide 151 and folded back for attachment. Similarly, a second strap guide 152 may be removably attached to the multi-region panel 153 via a secondary strap 164, which includes a "hook" type fastener (not shown). In particular, the second strap guide 152 may be configured to be removably attached to a posterior side 165 of the second lateral panel 159 and/or the posterior side 163 of the center panel 154. The secondary strap 164 may be inserted through an opening of the second strap guide 152 and folded back before attachment to the posterior side 165 of the second lateral panel 159 and/or the posterior side 163 of the center panel 154.

Furthermore, as shown in FIG. 1, each of the strap guides 151 and 152 is adapted with an aperture to enable corresponding third and fourth strap members 186 and 188 of the support harness 180 to be threaded there through and form loops 190 and 192 between a top region 148 of the spinal support extension 140 to their respective strap guides 151 and 152. Hence, the first and second strap members 182 and 184, which are attached to the third and fourth strap members 186 and 188, may be used as shoulder straps for the orthopedic brace 100. The third and fourth strap members 186 and 188 continue to propagate to a second pair of strap guides 170 and 175 (e.g., dual D-rings, etc.), where the strap members 186 and 188 are passed through first aperture 171 and 176 of the strap guides 170 and 175, folded onto themselves, and affixed by alligator end portions 172 and 177, respectively. Secondary straps 173 and 178 for securing the strap guides 170 and 175 to the belt brace 110 are looped through a second aperture 174 and 179 of the strap guides 170 and 175 and folded back for attachment to the brace belt 110.

Figure 2:
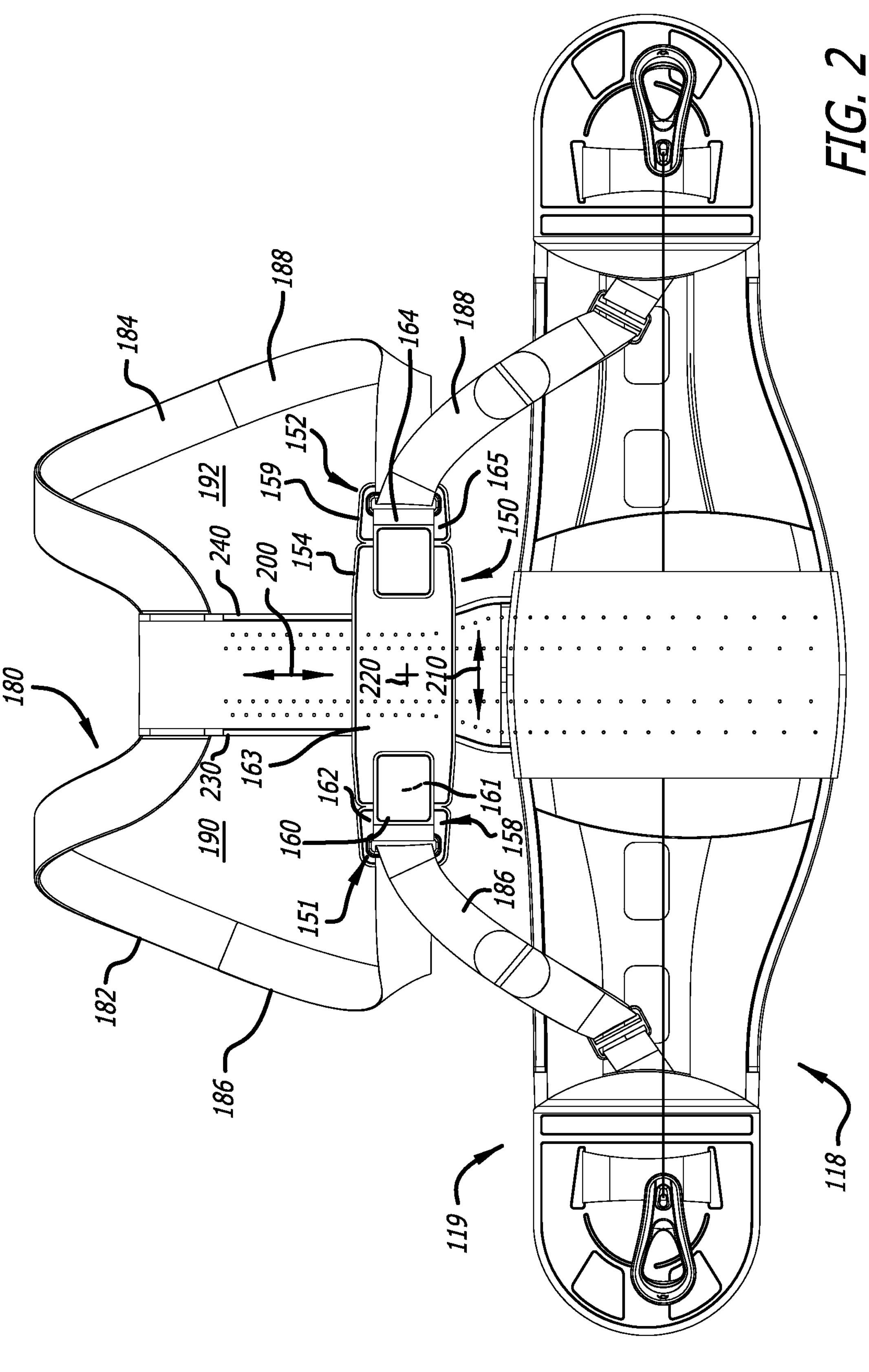
FIG. 2 is an exemplary embodiment of a rear-facing view of the orthopedic brace of FIG. 1 featuring a strap adjustment member of the support harness of FIG. 1.

Referring now to FIG. 2, an exemplary embodiment of a rear-facing view of the orthopedic brace 100 of FIG. 1, featuring the strap adjustment member 150 of the support harness 180, is shown. The strap adjustment member 150 operates as an interface to provide proper guidance between portions of the strap members 182/186 and 184/188 positioned on the anterior side 119 of the belt 110 and the strap members 186 and 188 positioned on the posterior side 118 of the belt 110.

As shown, the strap adjustment member 150 may be repositioned along a longitudinal (vertical) direction 200 to expand or restrict the diameter of the strap loops 190 and 192. Longitudinal movement of the strap adjustment member provides for vertical adjustability of the straps 182/186 and 184/188 to customize positioning of the straps to avoid impinging the axilla of the wearer. Similarly, the strap adjustment member 150 may be repositioned in a lateral (horizontal) direction 210 to effectuate change in the first strap loop 190 and inverse change in the second strap loop 192. For example, by shifting a center point 220 of the strap adjustment member 150 (located at the center panel 154) towards a first edge 230 of the spinal support extension 140, the lateral range of the first strap loop 190 is increased while the lateral range of the second strap loop 192 is decreased. Similarly, by shifting the center point 220 of the strap adjustment member towards a second edge 240 of the spinal support extension 140, the lateral range of the second strap loop 192 is increased while the lateral range of the first strap loop 190 is decreased. This second adjustment provides another means for positioning the straps to avoid impinging the axilla of the wearer.

Additionally, the secondary strap 160 associated with the first strap guide 151 may be removably attached to the center panel 154 and/or the first lateral panel 158 as the secondary strap 160 features its anterior side 161 with a "hook" type fastener (not shown) for attachment to the posterior side 162 of the first lateral panel 158 and/or a posterior side 163 of the center panel 154 having "loop" type fasteners. This ease in repositioning of the first strap guide 151 allows for further customization of the first strap loop 190 relative to its lateral (horizontal) positioning independent of the second strap loop 192.

Similarly, the secondary strap 164 associated with the second strap guide 152 may be removably attached to the center panel 154 and/or the second lateral panel 159 as the secondary strap 164 features its anterior side (not shown) with a "hook" type for attachment to the posterior side 165 of the second lateral panel 159 and/or the posterior side 163 of the center panel 154 having "loop" type fasteners. This ease in repositioning of the second strap guide 152 further allows customization of the second strap loop 192 without impinging on the first strap loop 190.

Figure 3A:
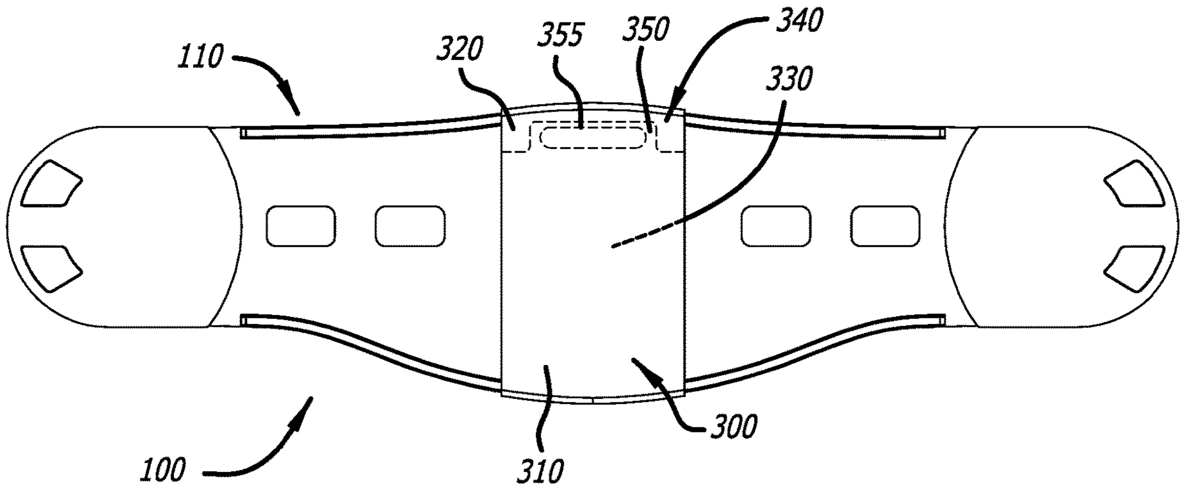
FIG. 3A is an exemplary embodiment of a front-facing view of the belt brace being a component of the orthopedic brace of FIG. 1 featuring a structural member for retention of the spinal support extension.
Figure 3B:
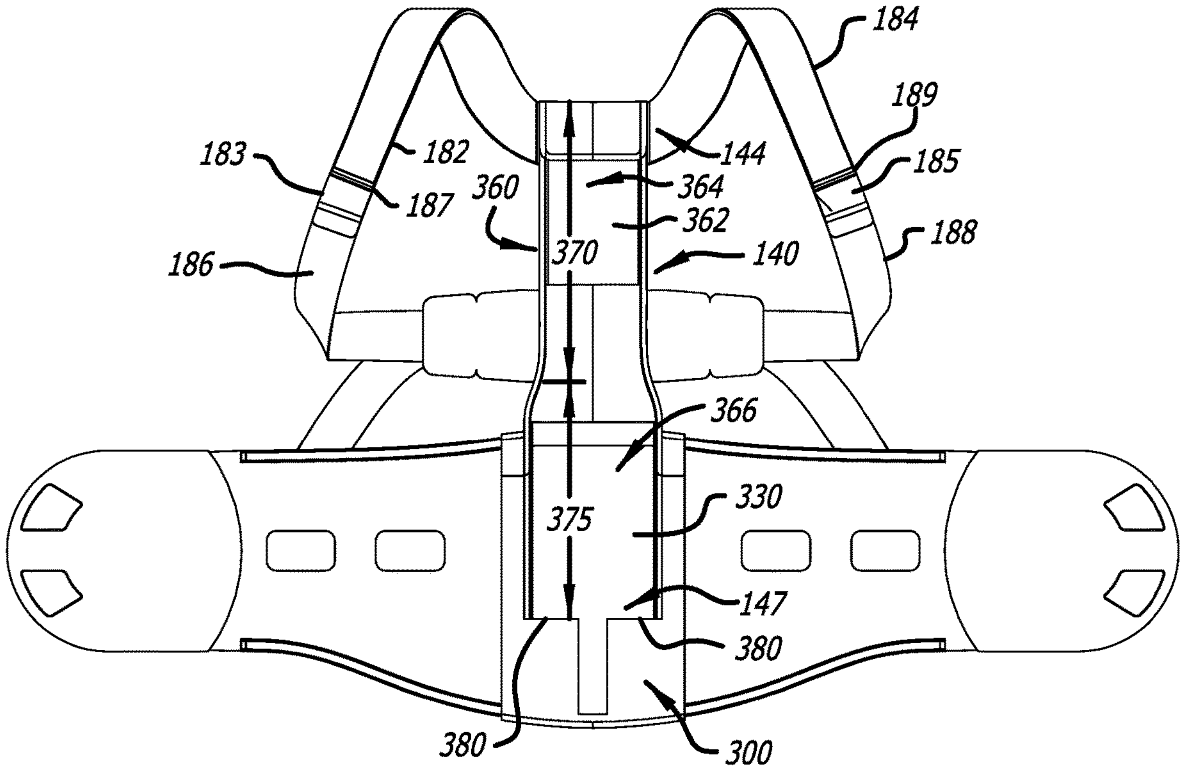
FIG. 3B is an exemplary embodiment of the front-facing view of the orthopedic brace of FIG. 1 featuring a more detailed view of the structural member of FIG. 3A.

Referring to FIG. 3A, an exemplary embodiment of a front-facing view of the belt brace 110 deployed within the orthopedic brace 100 of FIG. 1 is shown, where the belt brace 110 features the structural member 300, which is disposed on the lumbar support 112 of the belt brace 110 and configured to secure the spinal support extension 140. According to one embodiment of the disclosure, the structural member 300 is formed by two planar members 310 and 320 collectively forming a partially-enclosed, recessed area 330 between these planar members 310 and 320. As an illustrative example, each of the planar members 310 and 320 may include, but is not limited or restricted portions of soft goods that collectively form the partially-enclosed recessed area 330 as a pocket sized to receive the second end 147 of the spinal support extension 140 as shown in FIG. 3B. The soft goods forming the pocket 330 may corresponding to one or more layers of textiles, fabric (inclusive of woven fabrics and/or non-woven fabrics), or another material.

In particular, as shown in FIG. 3A, the pocket 330 is formed by aligning the first planar member 320 with the second planar member 330 and sealing their perimeter to leave an opening 340 at an upward facing portion of the perimeter unsealed. Proximate to the opening 340 of the pocket 330, a flap 350 may include a fastener 355 (e.g., a hook and loop fastener) to secure itself to a fastener located on an anterior surface 362 of a sleeve 360 of the spinal support extension 140 of FIG. 3B.

Referring now to FIG. 3B, an exemplary embodiment of the front-facing view of the orthopedic brace 100 of FIG. 1 is shown, with the belt brace 110 featuring the complementary pocket 330 for retaining the spinal support extension 140. As shown in detail in FIGS. 4A-4F, the spinal support extension 140 includes an adjustable strut positioned within the sleeve 360 having a contour in accordance with the shape of the adjustable strut. In particular, an upper portion 364 of the sleeve 360 (and adjustable strut), which is part of a top portion 370 of the spinal support extension 140 inclusive of the first end 144, has a narrower width than a lower portion 366 of the sleeve 360 (and adjustable strut), which is part a bottom portion 375 of the spinal support extension 140. The bottom portion 375 includes the second end 147 of the spinal support extension 140. This narrowing in width is designed to add comfort as the first end 144 of the spinal support extension 140 will reside between shoulder blades of the wearer.

After the adjustable strut has been set to a desired length and partially inserted into the sleeve 360, the bottom portion 375 of the spinal support extension 140 is at least partially inserted into the pocket 330. As a result, most (if not all) of the top portion 370 of the spinal support extension 140 resides outside of the pocket 330. A rigid ledge member 380 may be positioned within the pocket 330 to physically support the spinal support extension 140 (inclusive of an adjustable strut 400 or 500 and its corresponding sleeve 360) to avoid tearing of the soft goods forming the pocket 330.

III. Adjustable Strut—First Embodiment

Figure 4A:
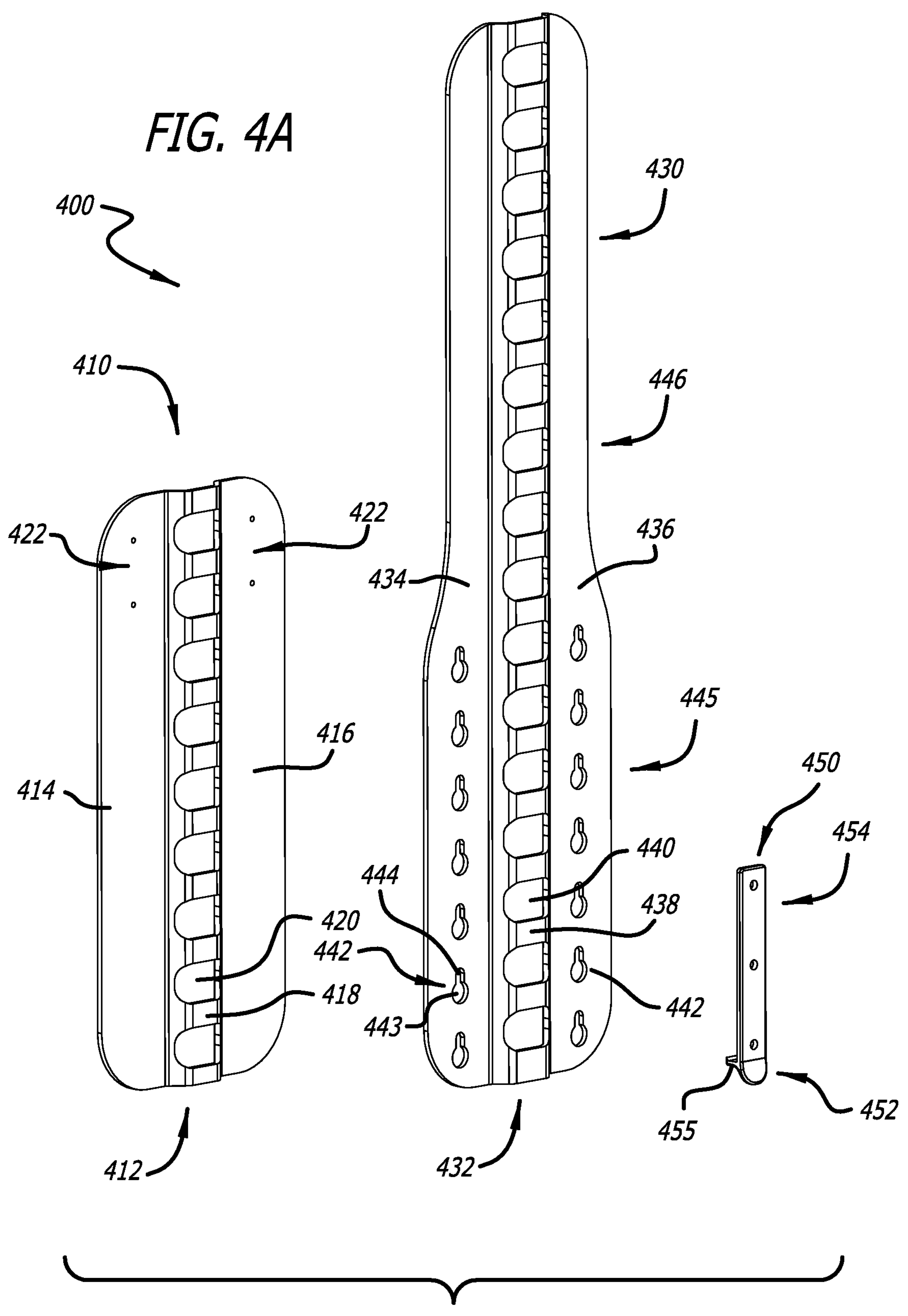
FIG. 4A is a first exemplary embodiment of a perspective view of the members forming an adjustable strut implemented as part of the spinal support extension of FIG. 1.

Referring now FIG. 4A, a first exemplary embodiment of a perspective view of the members forming an adjustable strut 400 implemented as part of the spinal support extension 140 of FIG. 1 is shown. Herein, according to this embodiment of the disclosure, the adjustable strut 400 includes a first strut member 410, a second strut member 430 and a release lever 450. With the general construction of the first strut member 410 being substantially equivalent to a first portion 445 of the second strut member 430 (e.g., same width with outer panels and center aperture series aligned), the first strut member 410 and the second strut member 430 may be slidably engaged, as shown in detail in FIGS. 4C-4D. The first strut member 410 and the second strut member 430 may be made of a rigid or highly rigid material, including a metal (e.g., aluminum, titanium, steel, etc.), hardened plastic, carbon fiber, or a composition of materials.

As shown in FIG. 4A, the first strut member 410 includes a channel 412 disposed between a first outer panel 414 and a second outer panel 416. A first plurality of lateral bands 418 are formed and extend over the channel 412 between the first outer panel 414 and the second outer panel 416, which produces a second plurality of apertures 420. This particular construction, inclusive of the channel 412 and lateral bands 418 to interconnect the first outer panel 414 and the second outer panel 416, is selected to reduce a total weight of the spinal support extension 140 as well as introduce slight lateral flexibility while still restricting lateral movement. Additionally, one or more fasteners (e.g., posts) 422 extend from and are mounted to each of the first outer panel 414 and the second outer panel 416. The posts 422 may be engaged with selected locking apertures 442 of the second strut member 430 when these strut members 410 and 430 are aligned in order to couple the first strut member 410 to the second strut member 430 and set the adjustable strut 400 to a desired length.

According to one embodiment of the disclosure, the second plurality of apertures 420 may be lesser in number than the first plurality of lateral bands 418. Also, according to one embodiment of the disclosure, the lateral bands 418 may be configured with an angular (arc) curvature so that, when aligned with lateral bands 438 of the second strut member 430, an engagement region (lip) 455 of the release lever 450 is capable of securing together one of the plurality of lateral bands 418 along with its corresponding (and aligned) lateral band 438.

Referring still to FIG. 4A, the second strut member 430 includes a channel 432 disposed between a third outer panel 434 and a fourth outer panel 436. A third plurality of lateral bands 438 are formed and extend over the channel 432 between the third outer panel 434 and the fourth outer panel 436, which produces a fourth plurality of apertures 440. The fourth plurality of apertures 440 may be lesser in number than the third plurality of lateral bands 438. This particular construction is similar to the first strut member 420, except for, inter alia, (i) a different contour and (2) deployment of locking apertures 442 within the first portion 445 of the second strut member 430 in lieu of post(s) 422.

As shown, each of the locking apertures 442 may correspond to keyhole apertures, each of which includes a first aperture area 443 of a first prescribed area and a second aperture area 444 of a second prescribed area. As the second prescribed area is lesser in diameter than the first prescribed area, a post 422 may be oriented to extend with the first prescribed area 443, and thereafter, is slidably engaged within a surface of the third outer panel 434 or the fourth outer panel 436 surrounding the second prescribed area 444. Also, while the width of the channel 432 remain the same as the channel 412 of the first strut member 410, the widths of the third and fourth outer panels 434 and 436 change. In particular, within the first portion 445 of the second strut member 430, the outer panels 434 and 436 are sized with a width consistent with the outer panels 414 and 416 of the first strut member 410. Between the first portion 445 and the second portion 446 of the second strut member 430, however, the widths of the outer panels 434 and 436 transition to a second (and lesser) width. The entire width of the second portion 446 of the second strut member 430 is configured to be lesser in distance than a distance is less than the shoulder blade of the wearer.

The release lever 450 includes the engagement lip 455 extends generally orthogonal from the release lever 450. The release lever 450 is mounted longitudinally onto one or more of the lateral bands 438 spanning the channel 432, with a first end 452 of the release lever 450 featuring the engagement lip 455 being directed away from a second portion 446 of the second strut member 430. Hence, the first end 452 of the release lever 450 is oriented downward while a second end 454 of the release lever 450 is oriented upward.

It is contemplated that the architecture of the first strut member 410 and the second strut member 430 is selected where the load between the struts members 410 and 430 is anticipated to be in compression. As a result, the compressive forces drive the posts 422 into the second prescribed area 444 (narrow end) of the keyhole apertures 442, further securing the attachment of the these strut members against sagittal plane loading by the lip on the posts (number) while resisting compression between these strut members 410 and 430.

However, if the load between the two strut members 410 and 430 is in tension as shown in FIGS. 5A-5F, the keyhole apertures 442 would be inverted (e.g., rotated 180 degrees) so that the second prescribed area 444 (narrow end) of the keyhole apertures 442 is facing downward and the release lever 450 would be re-oriented 180 degrees with its engagement lip facing upward. Upwardly directed tension forces would be managed by the posts 422 being pulled into the second prescribed areas 444 (narrow ends) of the keyhole apertures 442 thereby securing the two strut members 410 and 430 while resisting sagittal plane loading by the lips on the posts 422.

Figure 4B:
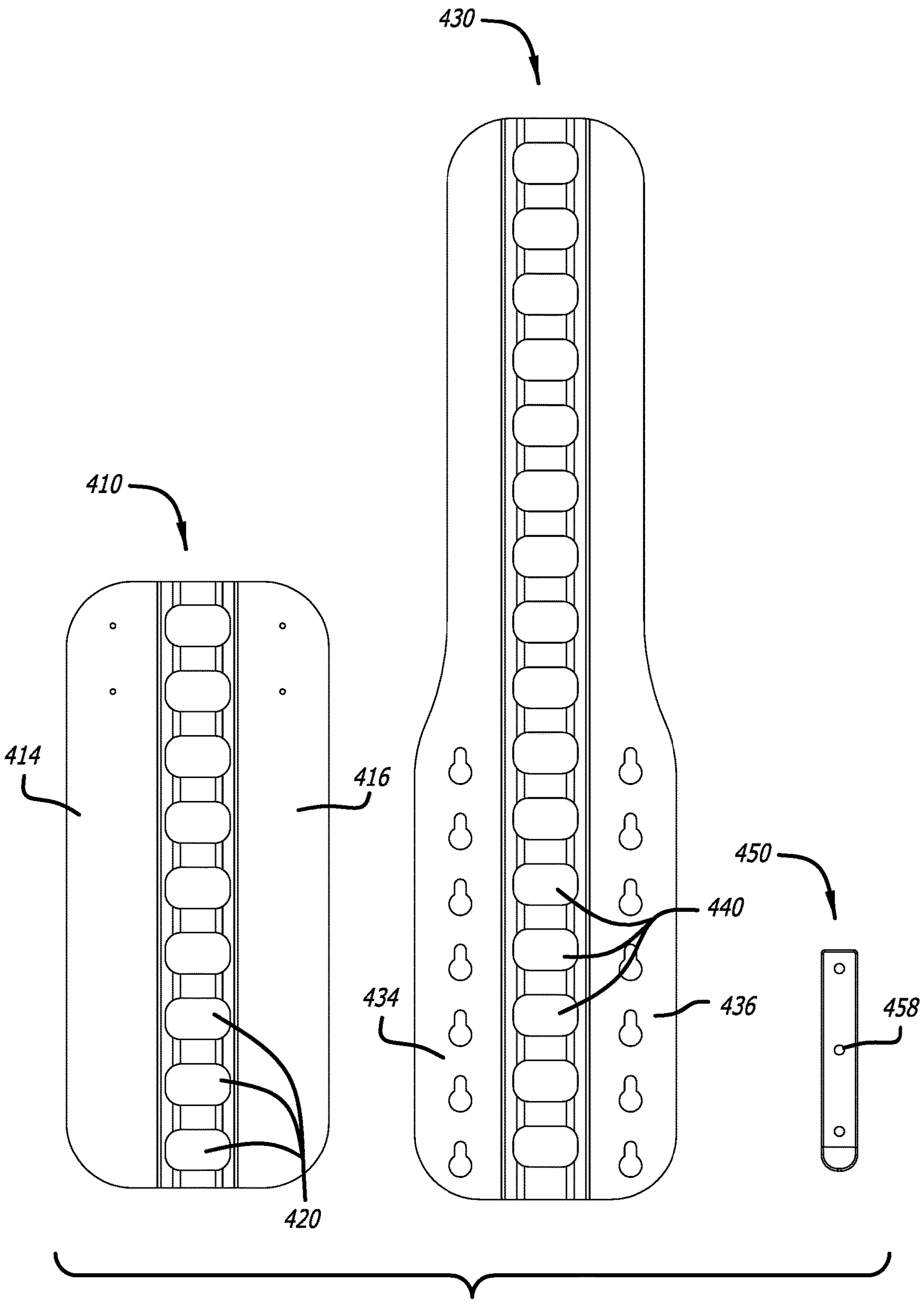
FIG. 4B is an exemplary embodiment of a plan view of the members forming the adjustable strut of FIG. 4A.

Referring now to FIG. 4B, an exemplary embodiment of a plan view of the members forming the adjustable strut of FIG. 4A. Herein, each of the second plurality of apertures 420 is identical or substantially consistent in shape and sizing as each of the fourth plurality of apertures 440. Moreover, the outer panels 414 and 416 of the first strut member 410 are identical or substantially consistent in shape (concur) and sizing a portion of the outer panels 434 and 436 of the second strut member 430.

Furthermore, according to one embodiment of the disclosure, the release lever 450 may be configured with predrilled apertures 458 into which a fastening member (e.g., screw, bolt, post, etc.) may be inserted for coupling to one or more of the lateral bands 438 of the second strut member 430. This may necessitate the generation of apertures in selected lateral band(s) 438 to receive the fastening member (s) as well.

Figure 4C:
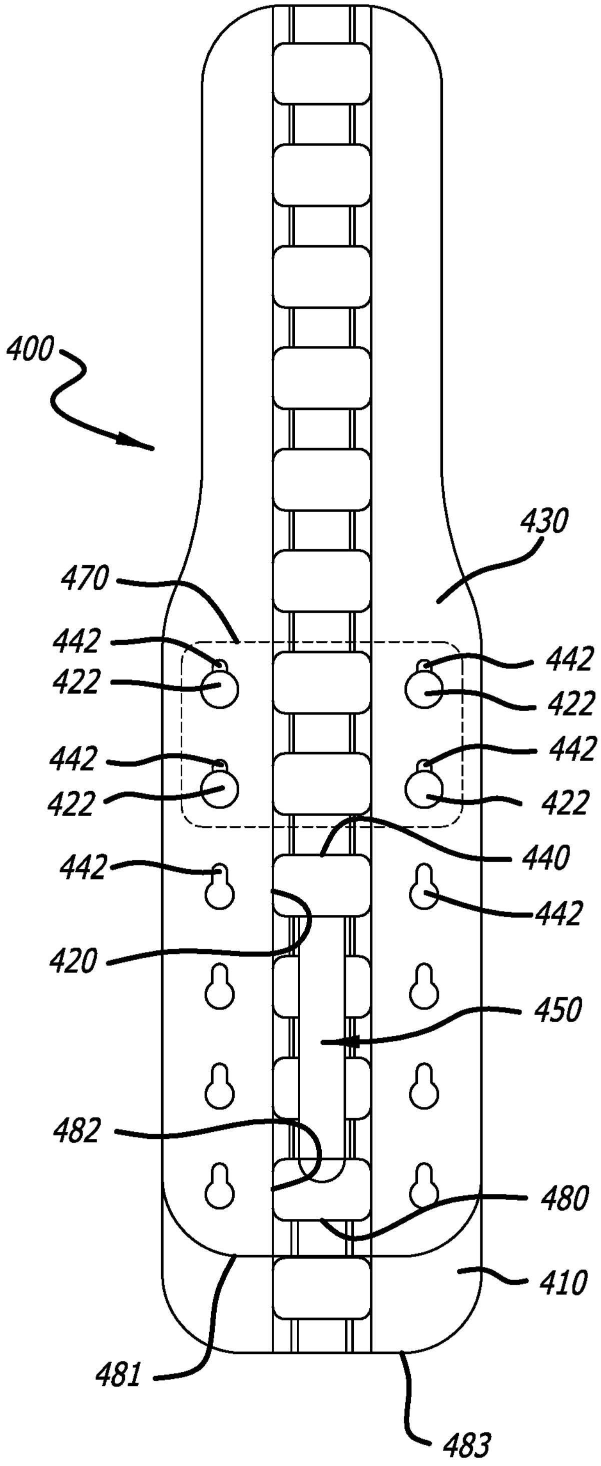
FIG. 4C is an exemplary embodiment of the adjustable strut of FIG. 4A positioned in a default (non-extended) state.

Referring now to FIG. 4C, an exemplary embodiment of the adjustable strut 400 of FIG. 4A positioned in a default (non-extended) state is shown. The adjustable strut 400 features the second strut member 430 aligned with and overlaying at least a portion of the first strut member 410. Both the apertures 420 of the first strut member 410 and the apertures 440 of the second strut member 430 are equivalent in size and shape as well as are arranged along their longitudinal center axes 460. As a result, when the second strut member 430 overlays the first strut member 410, the apertures 420 are aligned with a subset of the apertures 440.

After being set to a desired length, the posts 422 of the first strut member 410 are oriented to engage with a first subset 470 of the locking apertures 442. This subset 470 is located at the topmost of the locking apertures 442 so that the overall height (length) of the adjustable strut 400 is minimized. Herein, the release lever 450 is engaged with an aperture 480 of the fourth plurality of apertures 440 closest to a bottom edge 481 of the second strut member 430 and a second closest aperture 482 of the second plurality of apertures 420 to a bottom edge 483 of the first strut member 410.

Figure 4D:
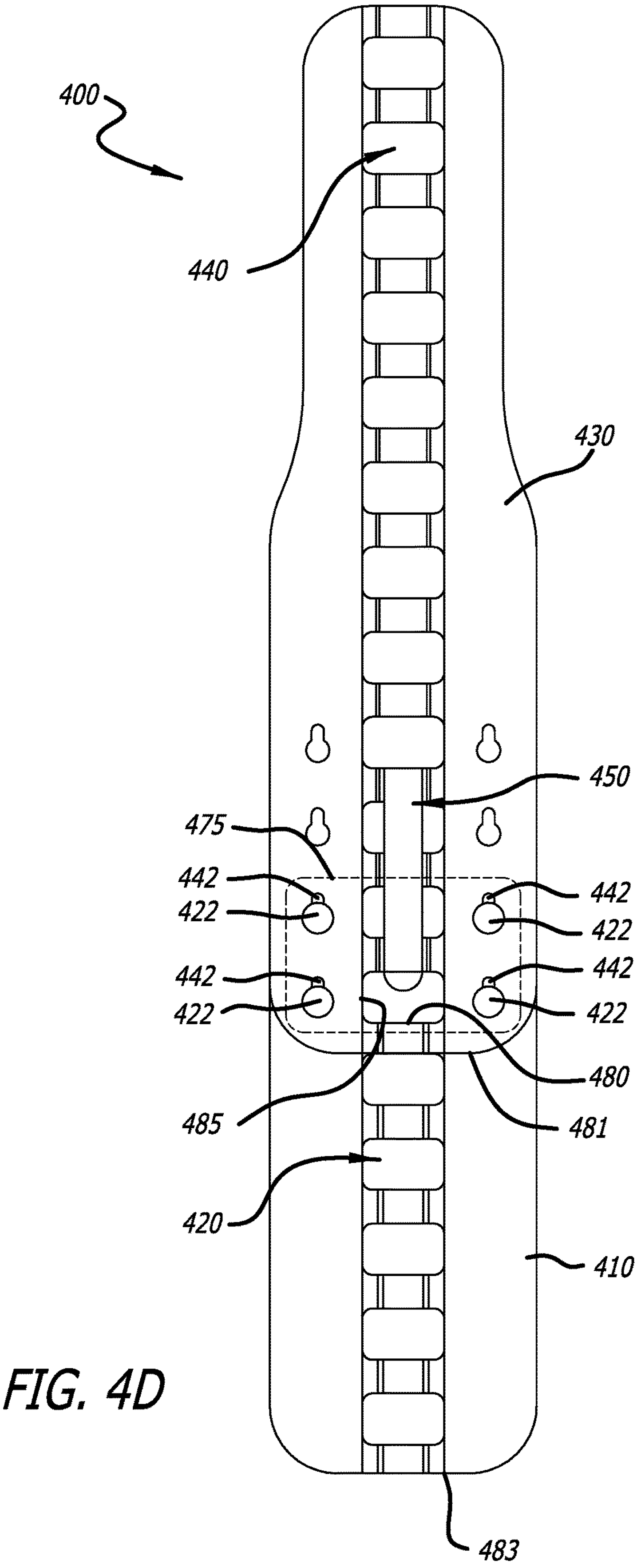
FIG. 4D is an exemplary embodiment of the adjustable strut of FIG. 4A positioned in an extended state.

Referring to FIG. 4D, an exemplary embodiment of the adjustable strut 400 of FIG. 4A positioned in an extended state is shown. Herein, the adjustable strut 400 features the second strut member 430 aligned with and overlaying at least a portion of the first strut member 410. Both the apertures 420 of the first strut member 410 and a subset of the apertures 440 of the second strut member 430 are aligned.

After being set to a desired length, the posts 422 of the first strut member 410 are oriented to engage with a second subset 475 of the locking apertures 442. The second subset of locking apertures 475 is located closest to the bottom edge 481 of the second strut member 430. As a result, the overall height (length) of the adjustable strut 400 is maximized as a greatest portion of the first strut member 410 is not overlayed by the second strut member 430. Herein, the release lever 450 is engaged with the aperture 480 of the fourth plurality of apertures 440 and an aperture 485 of the second plurality of apertures 420 further from the bottom edge 483 of the first strut member 410 than as illustrated in FIG. 4C (e.g. sixth aperture from bottom edge 483).

Figure 4E:
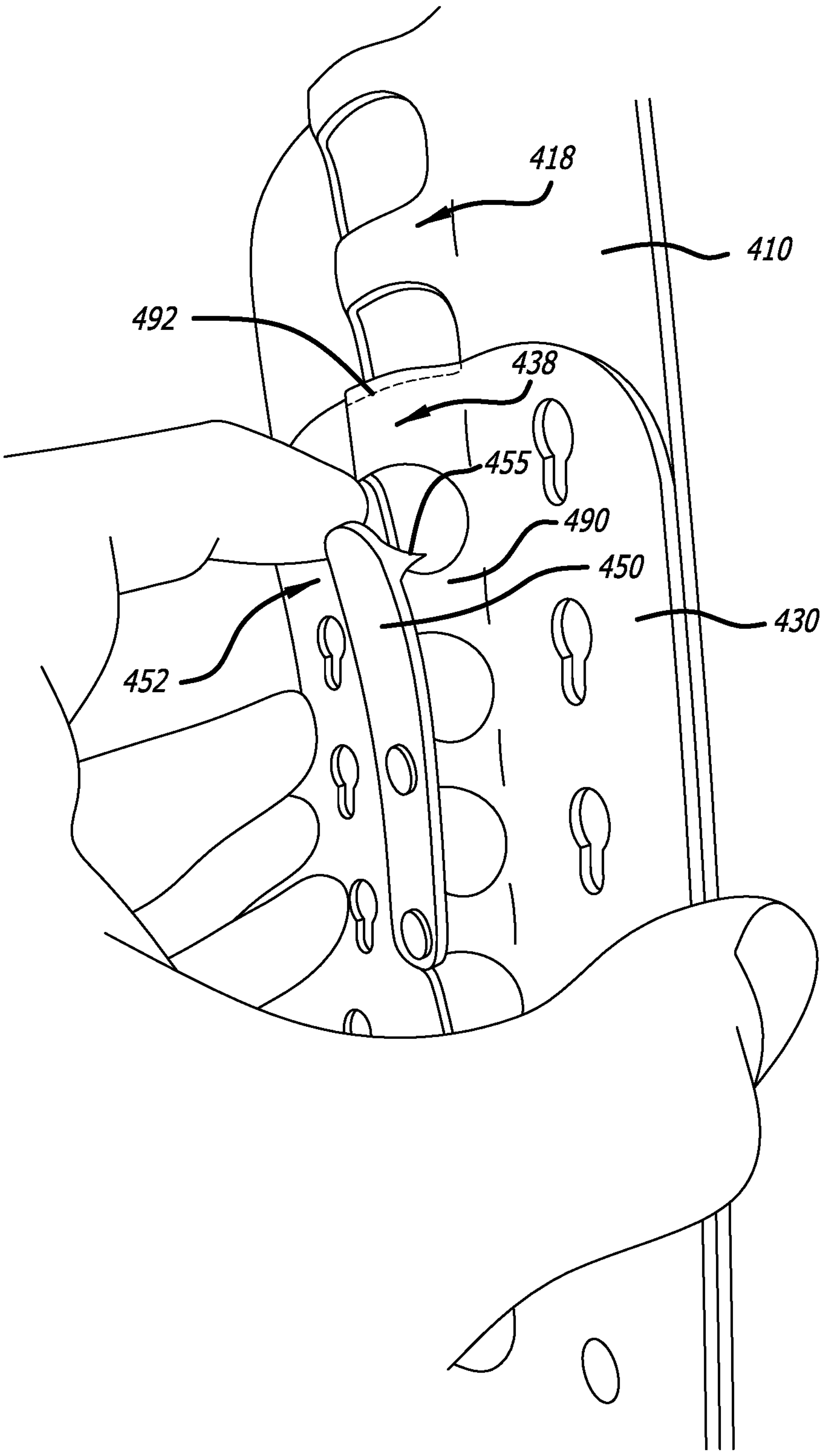
FIGS. 4E-4F illustrate an exemplary embodiment for height (length) alteration of the adjustable strut of FIG. 4A based on disengagement of both a release lever and posts mounted on a first strut member from locking apertures formed within a second strut member.
Figure 4F:
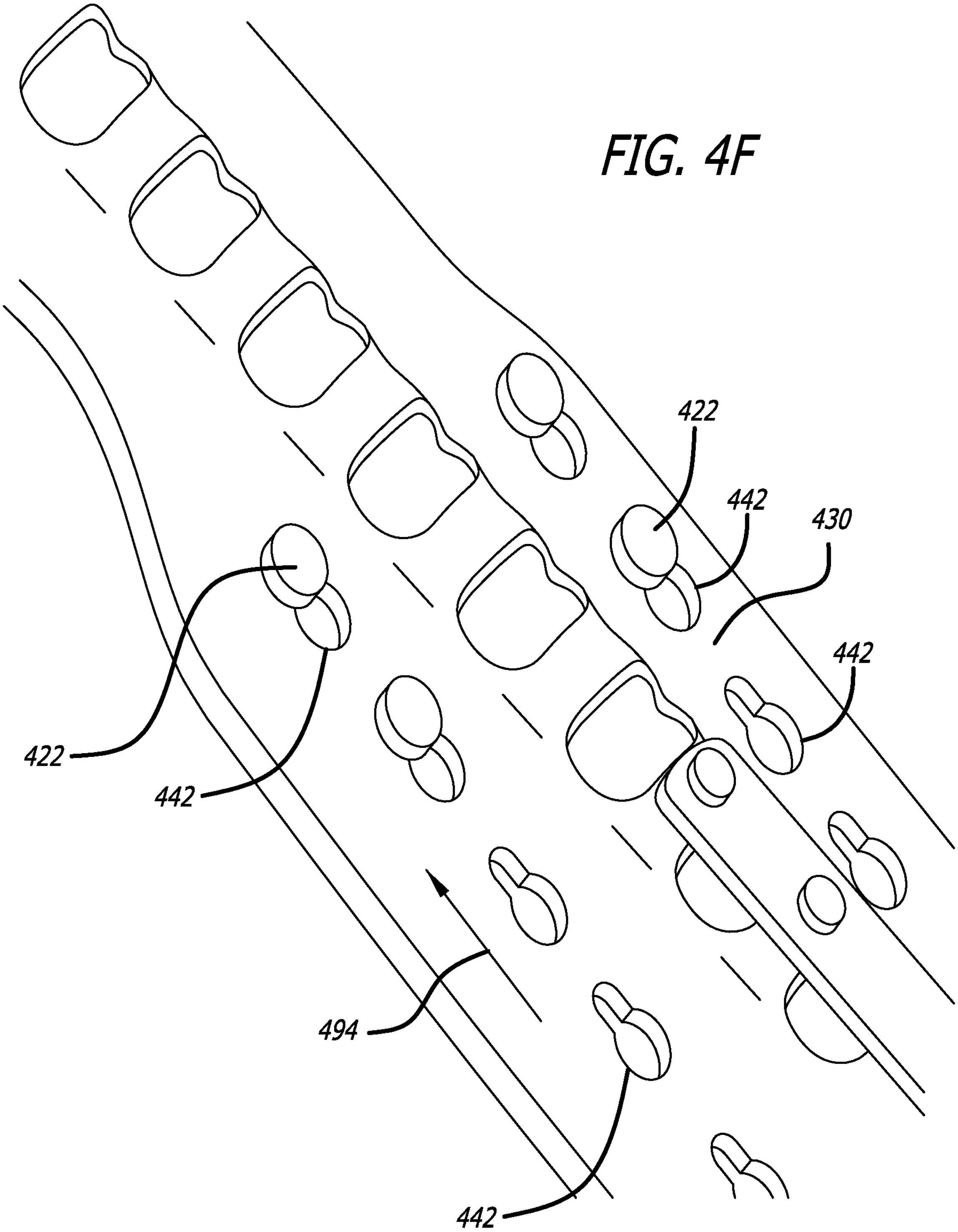

Referring to both FIGS. 4E-4F, an exemplary embodiment for height (length) alteration of the adjustable strut of FIG. 4A based on disengagement of both (i) the release lever 450 and (ii) the posts 422 mounted on the first strut member 410 from the locking apertures 442 is shown. Herein, in response to upward forces being applied to the first end 452 of the release lever 450, the engagement lip 455 disengages from a lateral band 490 of the lateral bands 438 associated with the second strut member 430 and a lateral band 492 of the lateral bands 418 associated with the first strut member 410. After disengaging, the second strut member 430 may be slid upward as represented by arrow 494 as shown in FIG. 4F, and thereafter, readjusted.

IV. Adjustable Strut—First Embodiment

Figure 5A:
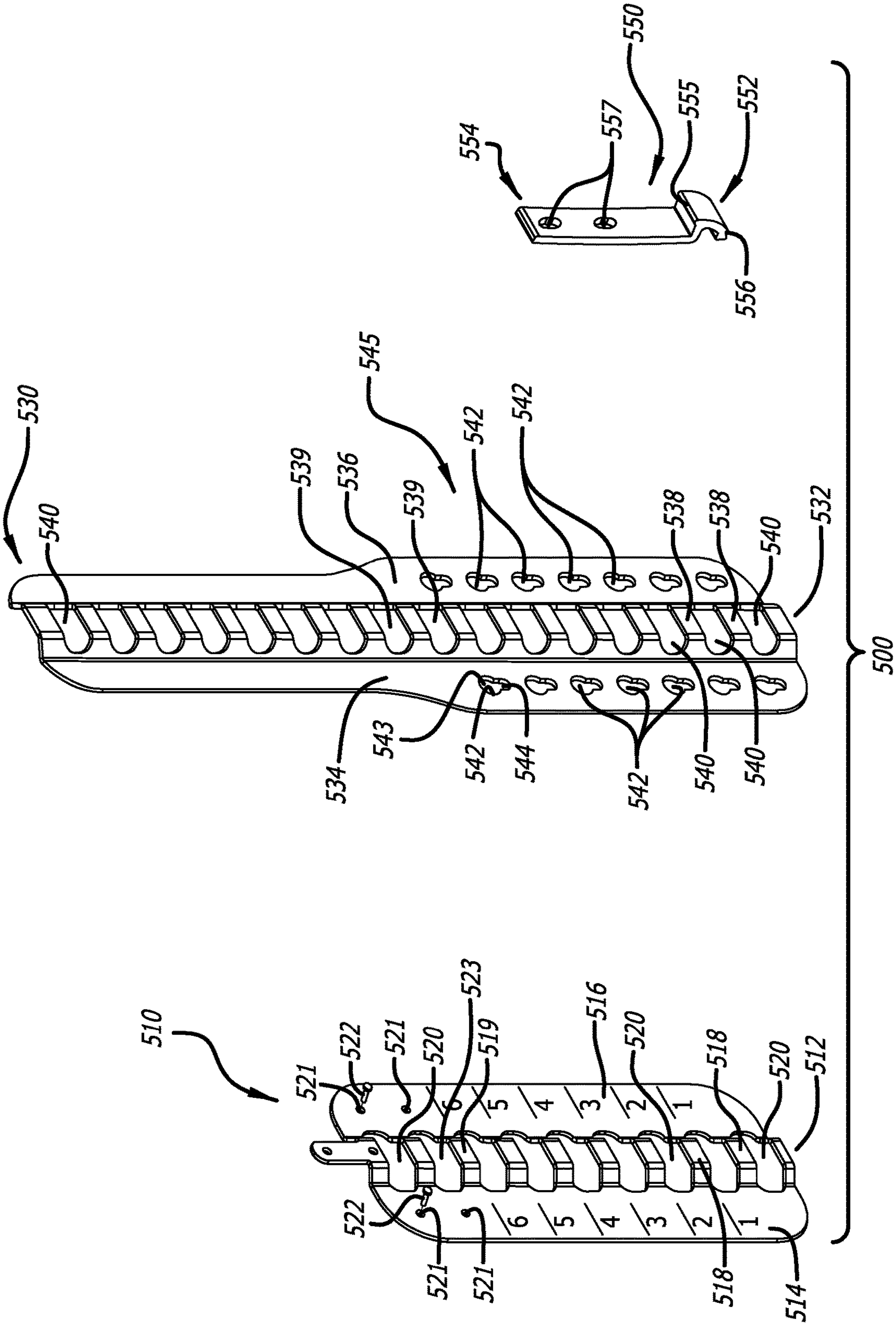
FIG. 5A is a second exemplary embodiment of a perspective view of the members forming an adjustable strut implemented as part of the spinal support extension of FIG. 1.

Referring now FIG. 5A, a second exemplary embodiment of a perspective view of members forming a second embodiment of the adjustable strut, referred to as "adjustable strut 500" and would be implemented as part of the spinal support extension 140 of FIG. 1, is shown. Herein, according to this embodiment of the disclosure, the adjustable strut 500 includes a first strut member 510, a second strut member 530 and a release lever 550. With the general construction of the first strut member 510 being substantially equivalent to a first portion 545 of the second strut member 530 (e.g., same general width with outer panels and center aperture series aligned), the first strut member 510 and the second strut member 530 may be slidably engaged, as shown in detail in FIGS. 5D-5F. The first strut member 510 and the second strut member 530 may be made of a rigid or highly rigid material, including a metal (e.g., aluminum, titanium, steel, etc.), hardened plastic, carbon fiber, or a composition of materials.

As shown in FIG. 5A, the first strut member 510 includes a channel 512 disposed between a first outer panel 514 and a second outer panel 516. A first plurality of lateral bands 518 are formed and extend over the channel 512 between the first outer panel 514 and the second outer panel 516, which produces a second plurality of apertures 520. This particular construction, inclusive of the channel 512 and lateral bands 518 to interconnect the first outer panel 514 and the second outer panel 516, is selected to reduce a total weight of the spinal support extension 140 of FIG. 1 as well as introduce slight lateral flexibility while still restricting lateral movement. Additionally, one or more posts 522 extend from and are mounted to each of the first outer panel 514 and the second outer panel 516 via post fastening apertures 521. The posts 522 may be engaged with selected locking apertures 542 of the second strut member 530 when these strut members 510 and 530 are aligned in order to couple the first strut member 510 to the second strut member 530 and set the adjustable strut 500 to a desired length.

According to one embodiment of the disclosure, the second plurality of apertures 520 may be lesser in number than the first plurality of lateral bands 518. Also, according to one embodiment of the disclosure, the lateral bands 518 may be configured with an angular (arc) curvature so that, when aligned with lateral bands 538 of the second strut member 530, a first engagement region 555 and a second engagement region 556 of the release lever 550 are collectively capable of securing together one of the plurality of lateral bands 518 along with its corresponding (and aligned) lateral band 538 as shown in FIGS. 5D-5E.

Referring still to FIG. 5A, the second strut member 530 includes a channel 532 disposed between a third outer panel 534 and a fourth outer panel 536. A third plurality of lateral bands 538 are formed and extend over the channel 532 between the third outer panel 534 and the fourth outer panel 536, which produces a fourth plurality of apertures 540. The fourth plurality of apertures 540 may be lesser in number than the third plurality of lateral bands 538. This particular construction is similar to the first strut member 520, except for, inter alia, (i) a different contour and (2) deployment of locking apertures 542 within the first portion 545 of the second strut member 530 in lieu of post(s) 522.

As shown, each of the locking apertures 542 may correspond to inverted keyhole apertures, each of which includes a first aperture area 543 with a first prescribed area and a second aperture area 544 with a second prescribed area lesser in diameter than the first prescribed area. The first aperture area 543 is positioned above the second aperture area 544. As the second aperture area 544 is lesser in diameter than the first aperture area 543, the post 522 may be oriented to extend with the first prescribed area 543, and thereafter, is slidably engaged within a surface of the third outer panel 534 or the fourth outer panel 536 surrounding the second prescribed area 544. Also, while the width of the channel 532 remain the same as the channel 512 of the first strut member 510, the widths of the third and fourth outer panels 534 and 536 change. In particular, within the first portion 545 of the second strut member 530, the outer panels 534 and 536 are sized with a width consistent with the outer panels 514 and 516 of the first strut member 510. Between the first portion 545 and the second portion 546 of the second strut member 530, however, the widths of the outer panels 534 and 536 transition to a second (and lesser) width. The entire width of the second portion 546 of the second strut member 530 is configured to be lesser in distance than a distance is less than the shoulder blade of the wearer.

The release lever 550 includes the first engagement region 555, which operates as a flange extending from a back surface 551 of a first end portion 552 of the release lever 550. The release lever 550 is mounted longitudinally onto a tab 525 extending generally orthogonal from a topmost lateral band 518, with the first end portion 552 of the release lever 550 featuring the second engagement region 555 to engage with a lower edge 539 of a selected lateral band of the third plurality of lateral bands 538, which functions as a top edge of a selected aperture of the fourth plurality of apertures 540 formed within the second strut member 530 to receive the first end portion 552. Hence, the first end portion 552 of the release lever 550 is oriented downward to extend through one of the second plurality of apertures 520 (e.g., aperture 523) for engagement with an edge of a lateral band forming a lower edge of the aperture 523 and an edge of one of the lateral bands 538 associated with an upper edge of a selected aperture of the fourth plurality of apertures 540. A second end portion 554 of the release lever 550 is oriented upward to be fixedly coupled to the tab 525 of the first strut member 510.

It is contemplated that the architecture of the first strut member 510 and the second strut member 530 is selected where the load between the struts members 510 and 530 is anticipated to be in tension. As a result, forces drive the posts 522 into the second prescribed area 544 (narrow end) of the inverted keyhole apertures 542, further securing the attachment of the these strut members while resisting sagittal plane loading by the lips on the posts 522.

Figure 5B:
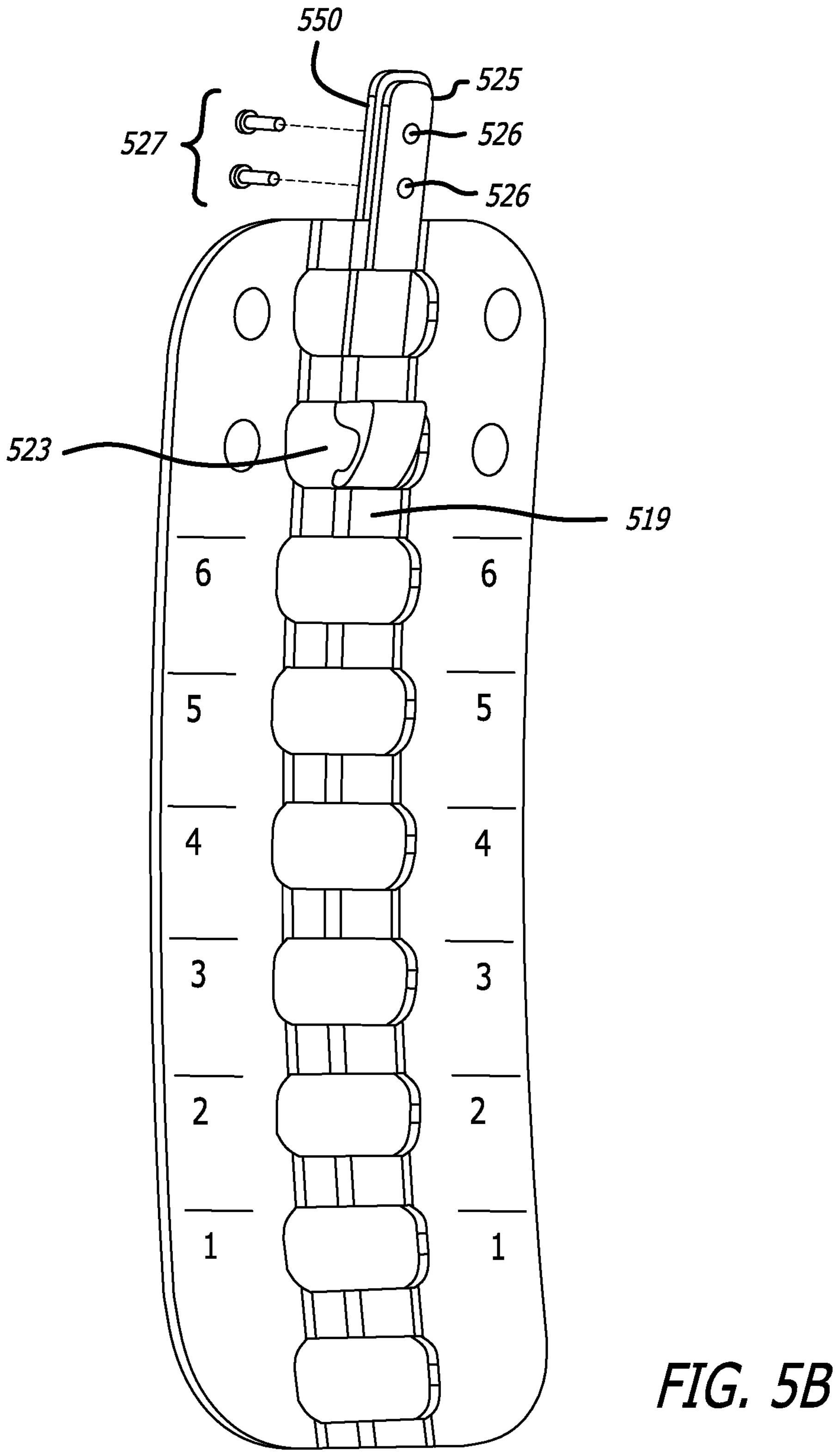
FIG. 5B is an exemplary embodiment of a front perspective view of the first strut member of FIG. 5A with the release lever of FIG. 5A coupled to a tab formed at an upper edge of the first strut member.

Referring now to FIG. 5B, an exemplary embodiment of a front perspective view of the first strut member 510 of FIG. 5A is shown, where the release lever 550 is coupled to the tab 525 formed at an upper edge 560 of the first strut member 510. As shown, the second end portion 554 of the release lever 550 is positioned under and aligned with the tab 525. The coupling of the release lever 550 to the tab 525 may be accomplished by fasteners 527 inserted through apertures 557 within the release lever 550 and apertures 526 within the tab 525.

According to one embodiment of the disclosure, the release lever 550 is fixedly coupled to the tab 525 of the first strut member 510. The first engagement region 555 of the release lever 550 is configured to extend through the aperture 523 for engagement with a lower edge of one of the selected lateral bands 538. The second engagement region 556 is configured to rest against an edge of a lateral band 519 being selected (based on the sizing of the release lever 550) from the lateral bands 518.

Figure 5C:
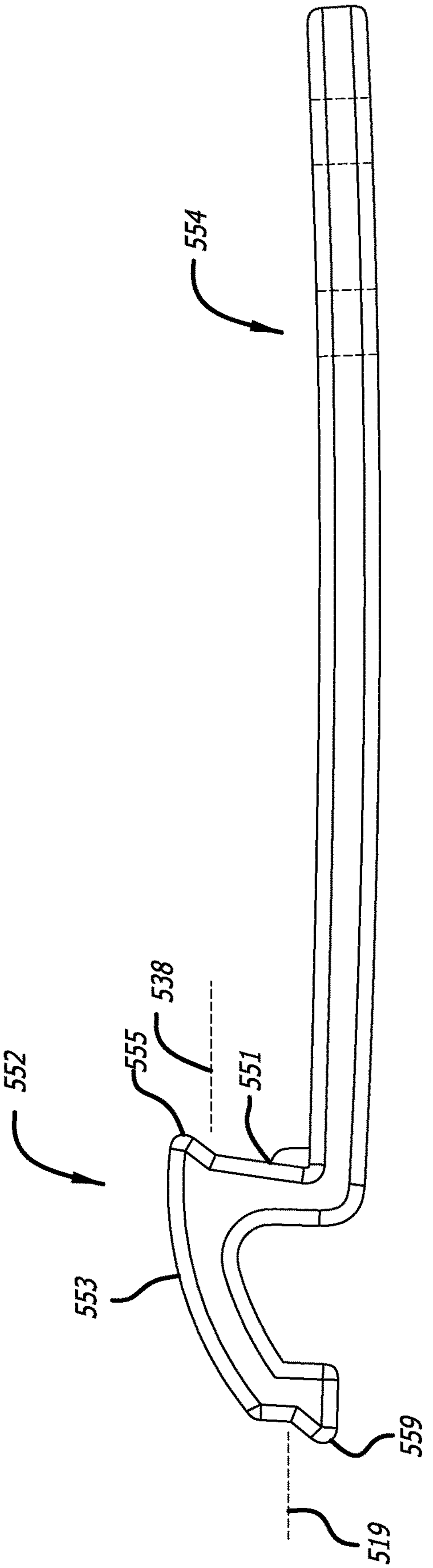
FIG. 5C is an exemplary embodiment of a side view of the release lever of FIG. 5A.
Figure 5D:
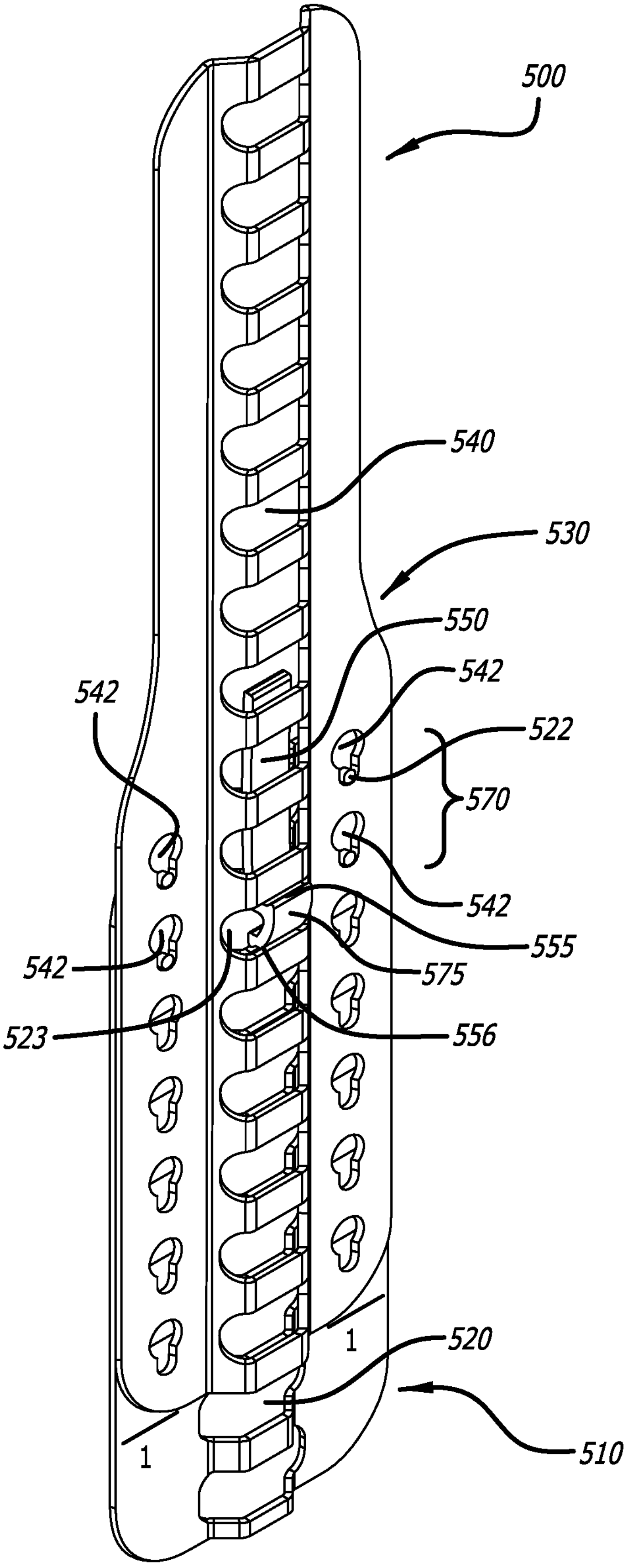
FIG. 5D is an exemplary embodiment of a front perspective view of the adjustable strut of FIG. 5A positioned in an extended state with the first strut member slidably coupled to the second strut member.
Figure 5E:
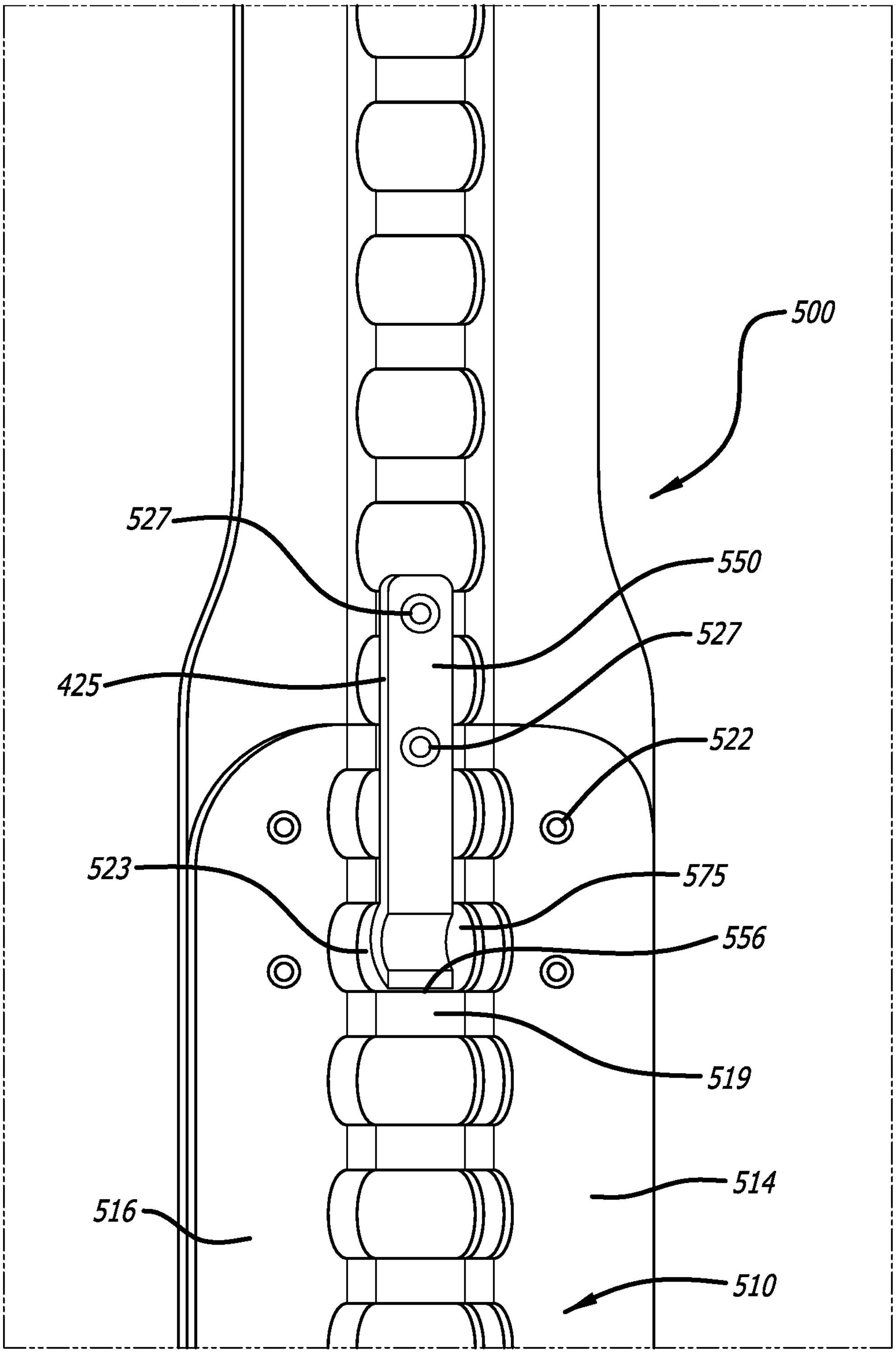
FIG. 5E is an exemplary embodiment of a back perspective view of the adjustable strut of FIG. 5A positioned in an extended state with the first strut member slidably coupled to the second strut member.

Referring to FIG. 5C, an exemplary embodiment of a side view of the release lever 550 of FIG. 5A is shown. Herein, the release lever 550 includes the first end portion 552 and the second end portion 554. The second end portion 554 is a planar segment coupled to the first end portion 552. The second end portion includes the apertures 557 sized for receipt of fasteners 527 of FIG. 5B for attachment to the tab 525 of the first strut member 510.

As further shown, the first end portion 552 includes the first engagement region 555 and the second engagement region 556. The first engagement region 555 operates so that an area between the back surface 551 and a first protruding (flange) portion 558 is shaped to receive an edge of a lateral band 538 of the second strut member 530 as represented by dashed lines (see also FIGS. 5D & 5F). Downward-biasing of the release lever 550 allows the first engagement region 555 to disengage from the second strut member 530 when a force is applied to a top surface 553 of the first end portion 552. The second engagement region 556 features a second protruding portion 559 to engage with an edge of a selected one of the lateral bands 518 (e.g., lateral band 519), which assists in securing the release lever 550 and preventing unwanted movement of the second strut member 530 relative to the first strut member 510.

Referring now to FIG. 5D, an exemplary embodiment of a front perspective view of the adjustable strut 500 of FIG. 5A positioned in an extended state is shown, where the first strut member 510 is slidably coupled to the second strut member 530. As shown, the adjustable strut 500 features the second strut member 530 aligned with and overlaying at least a portion of the first strut member 510. Both the apertures 520 of the first strut member 510 and the apertures 540 of the second strut member 530 are equivalent in size and shape as well as are arranged along shared longitudinal center axes. As a result, when the second strut member 530 overlays the first strut member 510, the apertures 520 are aligned with a subset of the apertures 540.

After being set to a desired length, the posts 522 associated with the first strut member 510 are oriented to engage with a first subset 570 of the locking apertures 542. For this illustrative embodiment, the subset 570 is located at the topmost of the locking apertures 542 so that the overall height (length) of the adjustable strut 500 is minimized. Herein, the release lever 550 is engaged with an aperture 575 of the fourth plurality of apertures 540 and the aperture 523 of the second plurality of apertures 520.

As shown in FIG. 5E, exemplary embodiment of a back perspective view of the adjustable strut 500 of FIG. 5E is shown. The fasteners 527 extend through the tab 425 and are affixed thereto. The posts 522 are affixed to the first outer panel 514 and the second outer panel 516 of the first strut member 510. The second engagement region 556 is positioned to rest against the selected lateral band 519. A majority of the release lever 550 is positioned under a backside of the first strut member 510.

Figure 5F:
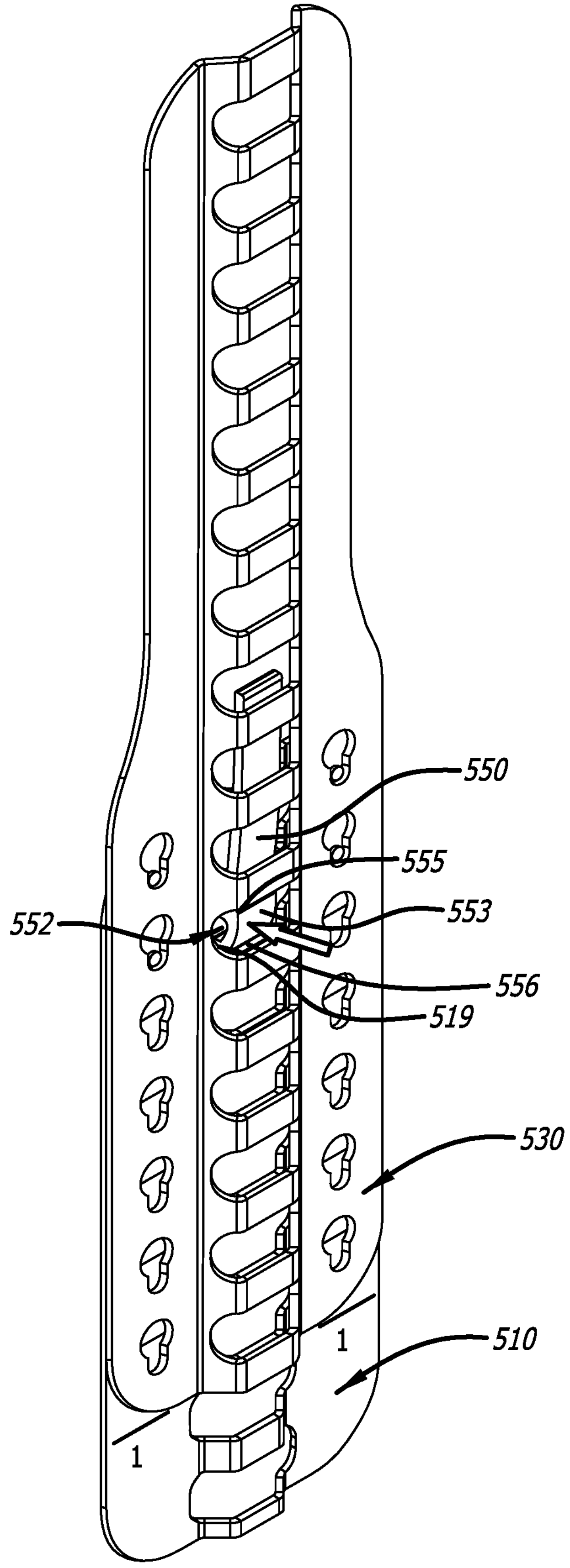
FIG. 5F is an exemplary embodiment of the adjustable strut of FIG. 5A with disengagement of the first strut member from the second strut member to allow for adjustment to the collective height of the adjustable strut.

Referring to FIG. 5F, an exemplary embodiment of the adjustable strut 500 of FIG. 5A is shown, with operations for disengagement of the first strut member 510 from the second strut member 530 to allow for adjustment to the collective height of the adjustable strut 500. Downward-biasing of the release lever 550 allows the first engagement region 555 to disengage from the second strut member 530 and the second engagement region 556 (not shown) to disengage from support by the lateral band 519 when a force is applied to the top surface 553 of the first end portion 552. This allows for further slidable adjustment in the length of the adjustable strut 500.

V. Orthopedic Brace with Adjustable Strut

Referring now to FIGS. 6A-6D, an exemplary embodiment associated with an installation of the adjustable strut 400 into the sleeve 360 and subsequent insertion into the pocket 330 arrange with the lumbar support 112 of the belt brace 110 is shown. According to FIG. 6A, the adjustable strut 400/500, namely the collection of the second strut member 430/530 overlaying and attached to the first strut member 410/510 (See FIGS. 4C-4D and/or FIGS. 5D-5E), is inserted into the sleeve 360. Given that the second strut member 430/530 has a contour that substantially encompassing the contour of the first strut member 410/510, the contour 600 of the sleeve 360 is consistent with the contour of the second strut member 430/530.

After being set to the desired length, the adjustable strut 400/500 may be partially inserted into the sleeve 360. Depending on the selected length, a portion of the adjustable strut 400/500, namely a portion 610 of the first strut member 410/510, may extend from the sleeve 360 prior to placement into (and covering by) the pocket 330. As shown, the sleeve 360 includes a tab 620 located on an anterior surface 630 of the sleeve 360 for insertion through at least an aperture of the first strut member 410/510 proximate to an edge 640 of the sleeve 360 or around the bottom edge 181 of the first strut member 410/510.

Figure 6A:
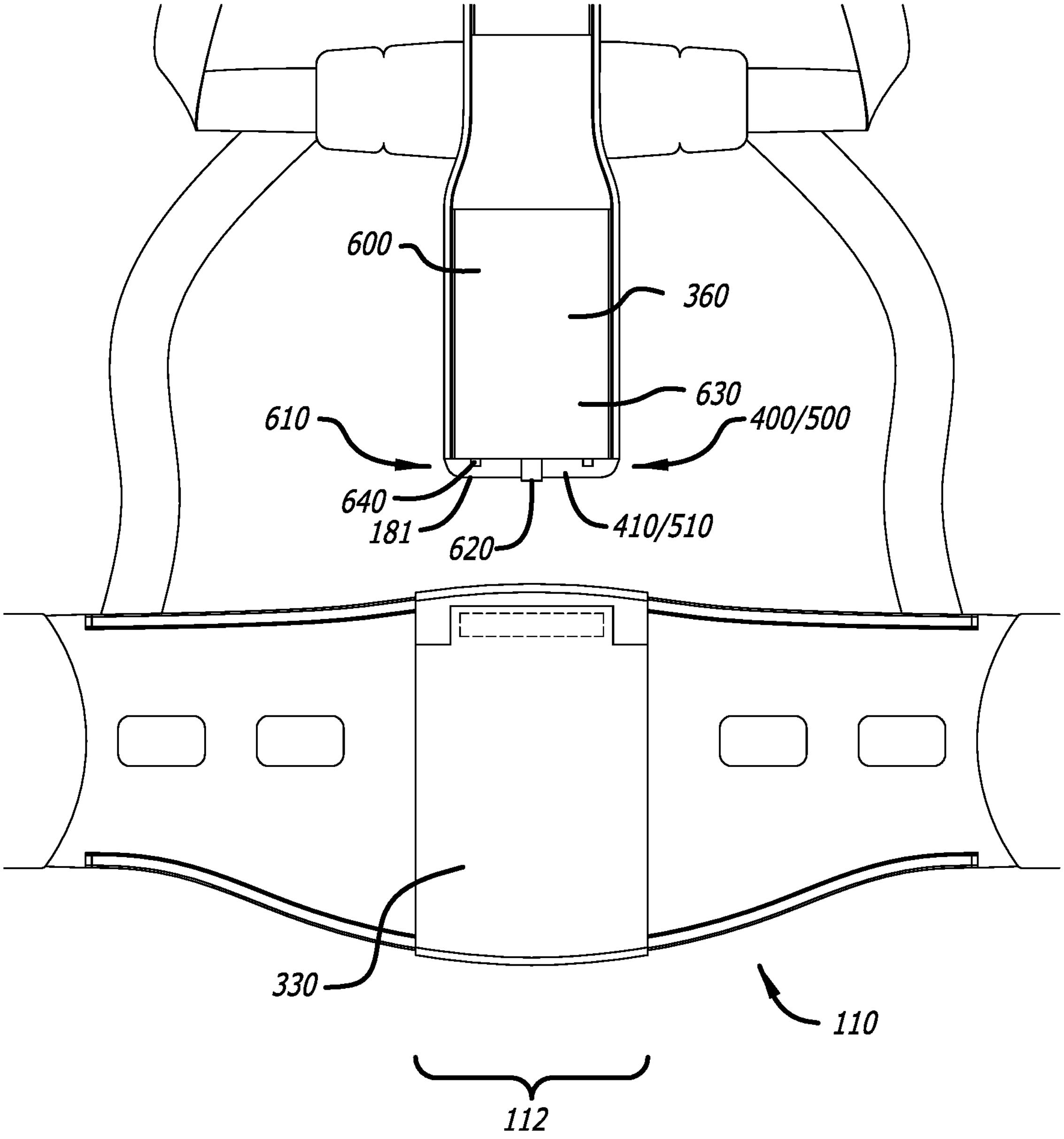
FIGS. 6A-6D illustrate an exemplary embodiment for installation of the adjustable strut into a sleeve and insertion of the sleeved, adjustable strut forming the spinal support extension into the structural member.
Figure 6B:
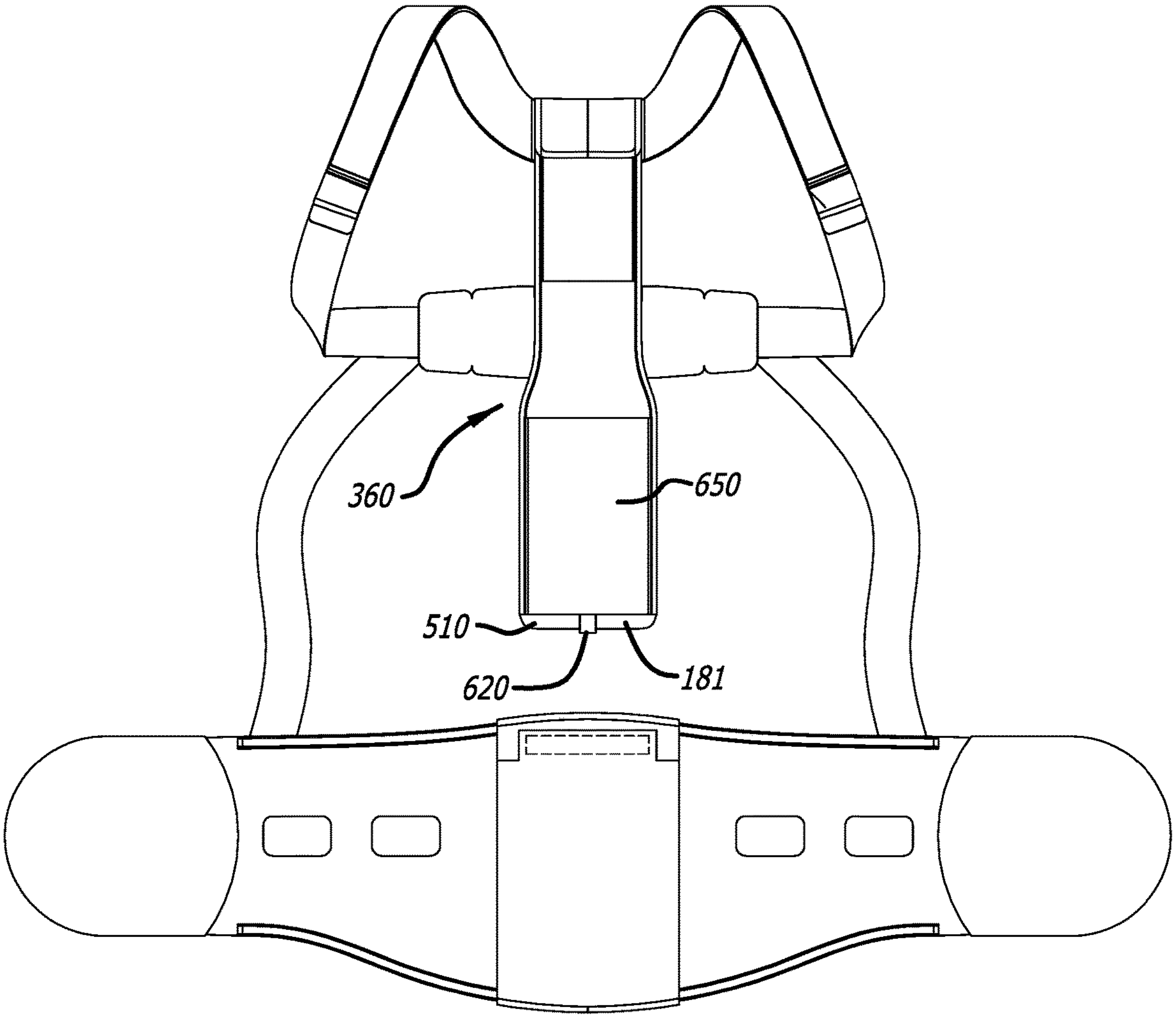

As shown in FIG. 6B, the tab 620 may be inserted through an aperture of the first strut member 410/510 (or around the bottom edge 181 of the first strut member 410/510) and attached to a posterior surface 650 of the sleeve 360. A portion of the tab 620 and a corresponding portion of the posterior surface 650 of the sleeve 360 may include complementary fasteners, such as complementary hook and loop fasteners for example.

Figure 6C:
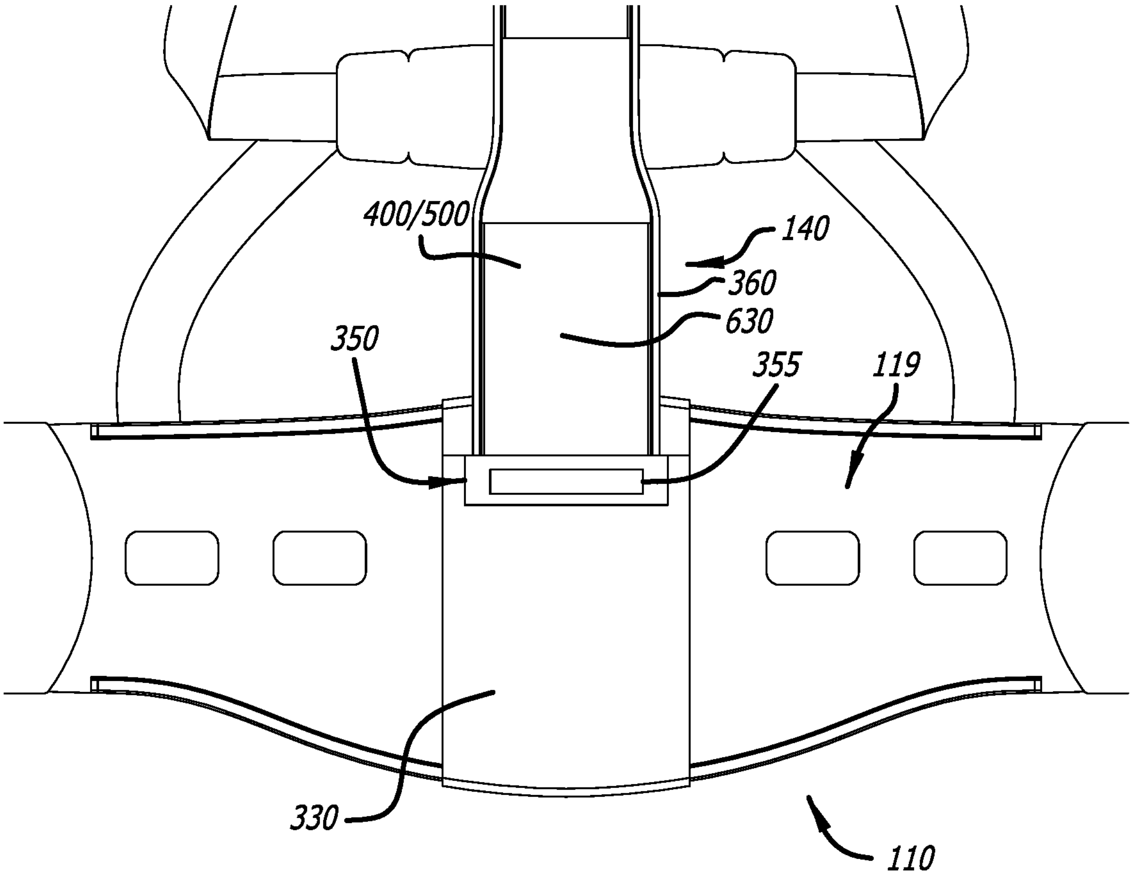
Figure 6D:
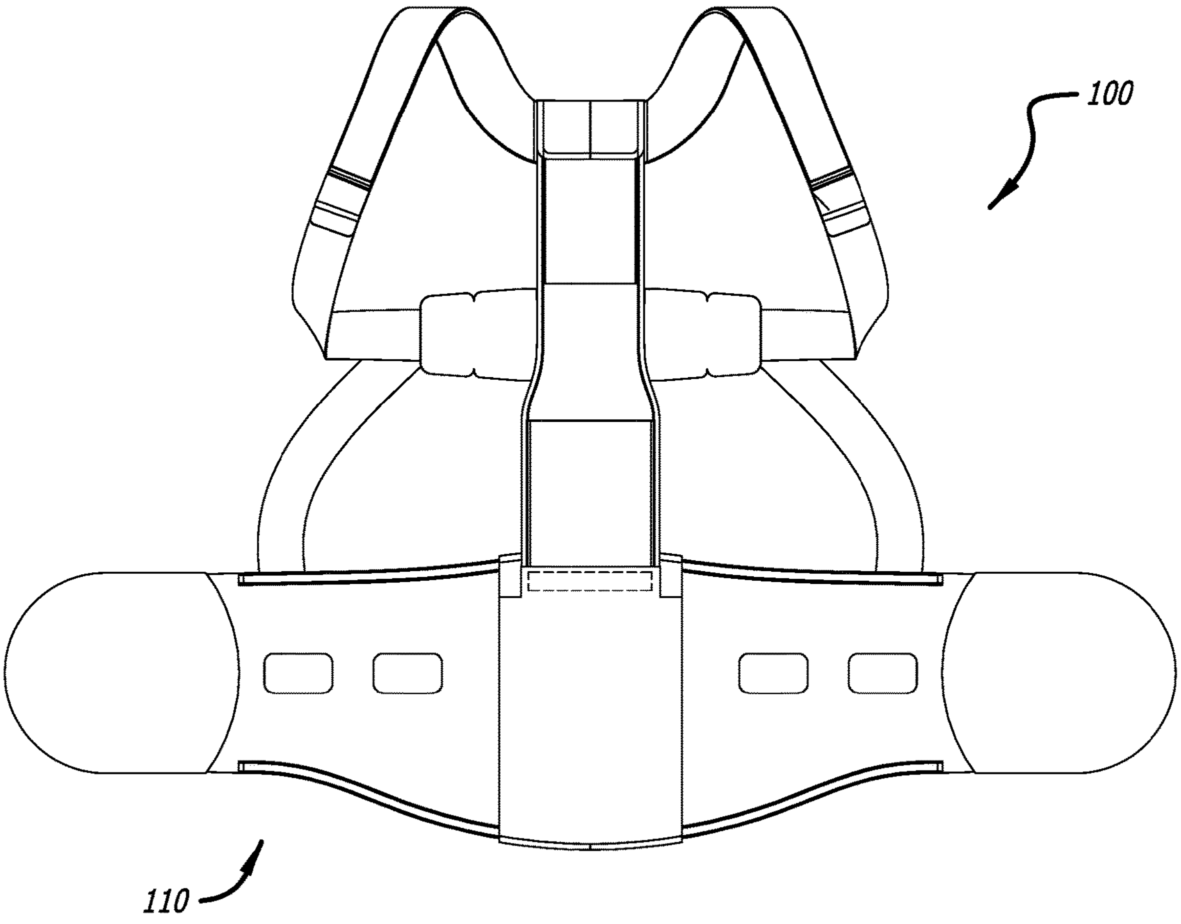

Referring now to FIG. 6C, the spinal support extension 140, including the adjustable strut 400/500 positioned within the sleeve 360, is placed within the pocket 330 positioned on the anterior side 119 of the belt brace 110. After insertion of the spinal support extension 140 into the pocket 330, the fastener 355 positioned on an inner surface of the flap 350 is attached to the anterior surface 630 of the sleeve 360. As a result, the brace belt 110 has been converted into a TLSO brace 100 as shown in FIG. 6D.

In the foregoing description, the invention is described with reference to specific exemplary embodiments thereof. However, it will be evident that various modifications and changes may be made thereto without departing from the broader spirit and scope of the invention as set forth in the appended claims.

What is claimed is:

1. An orthopedic brace comprising:

a belt brace including a structural member;

an adjustable spinal support extension inserted into the structural member, the spinal support extension comprises (i) a sleeve, (ii) a first strut member including a first channel, a first pair of panels positioned on opposite sides of the first channel, and a first plurality of lateral bands extending across the first channel to interconnect the first pair of panels, and (iii) a second strut member including a second channel, a second pair of panels positioned on opposite sides of the second channel, a second plurality of lateral bands extending across the second channel to interconnect the second pair of panels, wherein the second strut member is adjustably coupled to the first strut member to alter a length of the spinal support extension and retained at the length of the spinal support extension; and a release lever pivotally coupled to the second strut member, the release lever includes (i) a first end portion that comprises a first engagement region positioned facing downward and (ii) a second end portion fixedly coupled to the first strut member, wherein the first end portion is configured to (i) extend through or over an aperture of a first plurality of apertures for engagement with an edge of a first lateral band of the second plurality of lateral bands and (ii) is formed with a recessed area to receive and maintain the edge of a first lateral band of the second plurality of lateral bands, wherein the first strut member and the second strut member are partially enclosed within the sleeve and a fastener of the structural member is attachable to a fastener on the sleeve when the spinal support extension is placed within the sleeve.

2. The orthopedic brace of claim 1, wherein the release lever further includes a first end portion that comprises a second engagement region positioned facing upward and formed to create a recessed area to receive and maintain a lower edge of a second lateral band of the second plurality of lateral bands positioned immediately above the first lateral band of the second plurality of lateral bands.

3. The orthopedic brace of claim 2, a contour of the second strut member includes a first portion with each segment of the second pair of panels having a first width and a second portion with each segment of the second pair of panels having a second width being less than the first width.

4. The orthopedic brace of claim 3, wherein the first strut member includes one or more posts extending from each panel of the first pair of panels for engaging with locking apertures positioned within each corresponding panel of the second pair of panels when the second strut member is slidably engaged with the first strut member.

5. The orthopedic brace of claim 3, wherein the sleeve includes a tab extending from a bottom edge of a first side of the sleeve to pass through an aperture formed in at least two lateral bands of the first plurality of lateral bands, the tab includes a fastener for attachment to a fastener located on a second side of the sleeve opposite the first side of the sleeve.

6. The orthopedic brace of claim 1 operating as a thoraco-lumbo-sacral orthosis (TLSO) brace with the spinal support extension positioned along a mid-sagittal plane.

7. The orthopedic brace of claim 1 further comprising:

a strap adjustment member including a multi-region panel, the multi-region panel comprises a center panel disposed between lateral panels and each lateral panel includes a strap guide positioned on an outer edge of the lateral panel.

8. The orthopedic brace of claim 7, wherein the lateral panels of the multi-region panel are foldable toward the center panel.

9. The orthopedic brace of claim 1, wherein the spinal support extension extending from the belt brace and including a first end.

10. The orthopedic brace of claim 9 further comprising:

a support harness including a first strap member, a second strap member, a third strap member, and a fourth strap member, wherein the first strap member extends from the first end of the spinal support extension and is configured as a first knit tube including light weight, elastic material formed within an interior of the first knit tube, the second strap member extends from the first end of the spinal support extension in a direction substantially opposite to a direction of the first strap member, the second strap member is configured as a second knit tube including light weight, elastic material formed within an interior of the second knit tube, the third strap member is attached to and extends from an end of the first strap member, the third strap member possessing a different material composition and lesser thickness than the first strap member, and the fourth strap member is attached to and extends from an end of the second strap member, the fourth strap member possessing a different material composition and lesser thickness than the second strap member.

11. The orthopedic brace of claim 10 further comprising:

a strap adjustment member coupled to the support harness and removably coupled to an exterior surface of the spinal support extension, the strap adjustment member includes a multi-region panel, the multi-region panel comprises a center panel disposed between (i) a first lateral panel including a first strap guide positioned on an outer edge of the first lateral panel and (ii) a second lateral panel including a second strap guide positioned on an outer edge of the second lateral panel, wherein the third strap member is inserted through the first strap guide for subsequent attachment to the belt brace and the fourth strap member is inserted through the second strap guide for subsequent attachment to the belt brace.

12. An adjustable spinal support extension comprising:

a first strut member includes a first channel, a first pair of panels positioned on opposite sides of the first channel, a first plurality of lateral bands extending across the first channel to interconnect the first pair of panels, and at least one post extending from each panel of the first pair of panels;

a second strut member includes a second channel, a second pair of panels positioned on opposite sides of the second channel, a second plurality of lateral bands extending across the second channel to interconnect the second pair of panels, and a series of locking apertures formed in each panel of the second pair of panels sized to receive the at least one post; and a release lever pivotally coupled to the second strut member, the release lever includes a first engagement region formed at least by a protruding portion, wherein the first engagement region is facing downward and formed to create a recessed area to receive and maintain an edge of a first lateral band of the second plurality of lateral bands, wherein the release lever further includes a second end portion fixedly coupled to the first strut member, and a first end portion of the release lever extends over or through an aperture of a first plurality of apertures for engagement with the edge of the first lateral band of the second plurality of lateral bands, and wherein the second strut member being positioned to overlay the first strut member and slidably coupled together when each of the at least one post engages with a corresponding locking aperture of the series of locking apertures to set and retain a length of the spinal support extension formed by the second strut member overlaying the first strut member during usage.

13. The adjustable spinal support extension of claim 12, wherein a contour of the second strut member includes a first portion with each segment of the second pair of panels having a first width and a second portion with each segment of the second pair of panels having a second width being less than the first width.

14. The adjustable spinal support extension of claim 12, wherein the release lever further includes a second engagement region positioned facing upward and formed to create a recessed area to receive and maintain a lower edge of a second lateral band of the second plurality of lateral bands that is positioned immediately above the first lateral band of the second plurality of lateral bands.

15. The adjustable spinal support extension of claim 14, wherein the lower edge is a top edge for a selected aperture formed between neighboring lateral bands of the second plurality of lateral bands corresponding to the first lateral band and the second lateral band of the second plurality of lateral bands.

16. The adjustable spinal support extension of claim 12 deployed within a sleeve being part of an orthopedic brace, wherein the sleeve includes a tab extending from a bottom edge of a first side of the sleeve to pass through an aperture formed in at least two lateral bands of the first plurality of lateral bands, the tab includes a fastener for attachment to a fastener located on a second side of the sleeve opposite the first side of the sleeve.

17. The adjustable spinal support extension of claim 12, wherein the first plurality of lateral bands extending across the first channel align with the second plurality of lateral bands extending across the second channel when the second strut member is positioned to overlay the first strut member.

18. An orthopedic brace comprising:

a belt brace including a structural member;

an adjustable spinal support extension inserted into the structural member, the spinal support extension comprises (i) a sleeve, (ii) a first strut member including a first channel, a first pair of panels positioned on opposite sides of the first channel, a first plurality of lateral bands extending across the first channel to interconnect the first pair of panels, and one or more posts extending from each panel of the first pair of panels, and (iii) a second strut member including a second channel, a second pair of panels positioned on opposite sides of the second channel, a second plurality of lateral bands extending across the second channel to interconnect the second pair of panels and one or more locking apertures within each corresponding panel of the second pair of panels, wherein the second strut member is adjustably coupled to the first strut member to alter a length of the spinal support extension and retain at the length of the spinal support extension;

a release lever pivotally coupled to the second strut member, the release lever includes a first end portion and a second end portion fixedly coupled to a tab extending from the first strut member, wherein the first end portion comprises a first engagement region positioned facing downward and formed to create a recessed area to receive and maintain an edge of a first lateral band of the second plurality of lateral bands and the first end portion extends over or through an aperture of a first plurality of apertures for engagement with the edge of the first lateral band of the second plurality of lateral bands; and a strap adjustment member configured to be affixed to the sleeve of the spinal support extension, the strap adjustment member includes a multi-region panel, the multi-region panel comprises a center panel disposed between lateral panels each lateral panel includes a strap guide positioned on an outer edge of the lateral panel; and a support harness including a first strap member, a second strap member, a third strap member, and a fourth strap member, wherein the first strap member extends from a first end of the spinal support extension and is configured as a first knit tube including light weight, elastic material formed within an interior of the first knit tube, the second strap member extends from the first end of the spinal support extension in a direction substantially opposite to a direction of the first strap member, the second strap member is configured as a second knit tube including light weight, elastic material formed within an interior of the second knit tube, the third strap member is attached to and extends from an end of the first strap member, the third strap member possessing a different material composition and lesser thickness than the first strap member, the fourth strap member is attached to and extends from an end of the second strap member, the fourth strap member possessing a different material composition and lesser thickness than the second strap member, and the first strut member and the second strut member are partially enclosed within the sleeve and a fastener of the structural member is attachable to a fastener on the sleeve when the spinal support extension is placed within the sleeve.

* * * * *